United States Patent [19]

Eichelberger et al.

[11] 4,047,890
[45] Sept. 13, 1977

[54] METHOD AND APPARATUS FOR DETERMINING DEFICIENCIES IN ENZYMATIC REACTORS PARTICULARLY CLOTTING FACTOR LEVELS IN BLOOD PLASMAS

[75] Inventors: James W. Eichelberger, Plainfield, N.J.; Frederick M. Kent, Warrington; Michael Sokol, Abington, both of Pa.

[73] Assignee: Bio/Data Corporation, Willow Grove, Pa.

[21] Appl. No.: 560,464

[22] Filed: Mar. 21, 1975

Related U.S. Application Data

[63] Continuation-in-part of Ser. No. 411,994, Nov. 1, 1973, abandoned.

[51] Int. Cl.² .................... G01N 33/16; G06F 15/42
[52] U.S. Cl. ............... 23/230 B; 23/253 R; 235/151.35
[58] Field of Search .......... 23/230 B, 253 R; 250/564, 565; 73/64.1; 328/117; 307/233 A; 235/151.35; 346/33 ME

[56] References Cited

U.S. PATENT DOCUMENTS

| 3,307,392 | 3/1967 | Owen et al. .................. 73/64.1 |
| 3,419,879 | 12/1968 | Pelavin ..................... 346/33 ME |
| 3,458,287 | 7/1969 | Gross et al. .................. 23/230 B |
| 3,633,012 | 1/1972 | Wilhelmson ................ 235/151.35 |
| 3,658,480 | 4/1972 | Kane et al. .................. 23/230 B |
| 3,699,948 | 10/1972 | Ota et al. .................... 346/33 ME |
| 3,734,620 | 5/1973 | Cade ....................... 250/565 X |
| 3,754,866 | 8/1973 | Ritchie et al. ............... 23/230 B X |
| 3,769,178 | 10/1973 | Rothermel, Jr. .............. 23/230 R |
| 3,801,806 | 4/1974 | Denney ..................... 235/151.35 |
| 3,819,276 | 6/1974 | Kiess et al. .................. 23/253 R |
| 3,833,864 | 9/1974 | Kiess et al. .................. 73/64.1 X |
| 3,875,395 | 4/1974 | Jilek ........................ 23/253 R |

OTHER PUBLICATIONS

Glassman et al., "Fibrinogen Determinations; An Automated Photoelectric System," presented at the American Society of Clinical Pathologists, Spring Meeting, Feb. 1972, Atlanta, Georgia, four pages.
Clinical Diagnosis by Laboratory Methods — Todd — Stanford, pp. 394–428 ©, 1969.
Gradwohl's Clinical Laboratory Methods & Diagnosis; Frankel et al., vol. I, 7th Edit., 1970.

*Primary Examiner*—Morris O. Wolk
*Assistant Examiner*—Michael S. Marcus
*Attorney, Agent, or Firm*—Seidel, Gonda & Goldhammer

[57] ABSTRACT

The peak value of the first derivative of the optical density time curve is related to individual clotting factor levels, deficient or elevated. The relationship is logarithmic for all factors except fibrinogen and it is linear for fibrinogen. The apparatus and process disclosed herein apply the relationship to determine blood clotting factor levels.

12 Claims, 37 Drawing Figures

LOG-LOG PLOT OF THE PEAK VALUES OF THE CURVES SHOWN IN FIG. 3

FACTOR IX, PERCENT

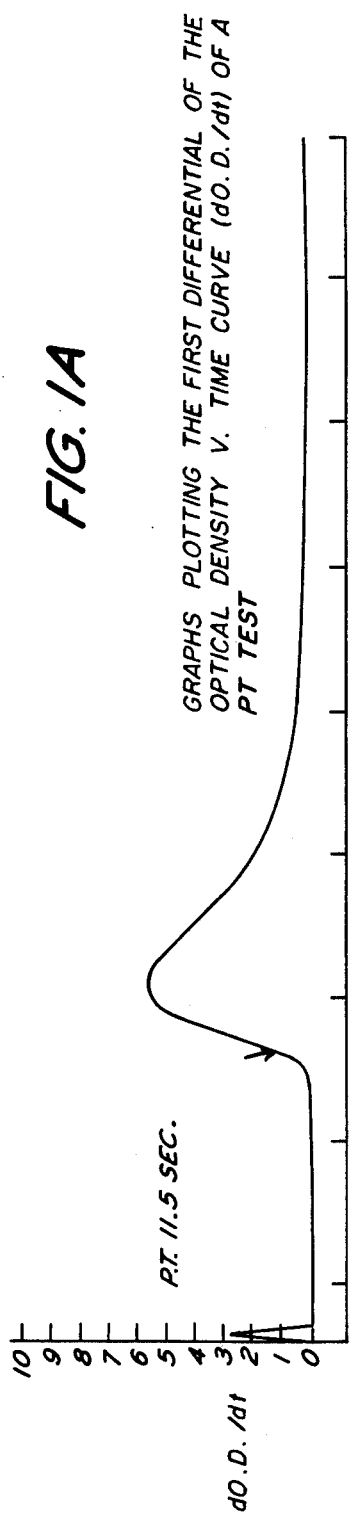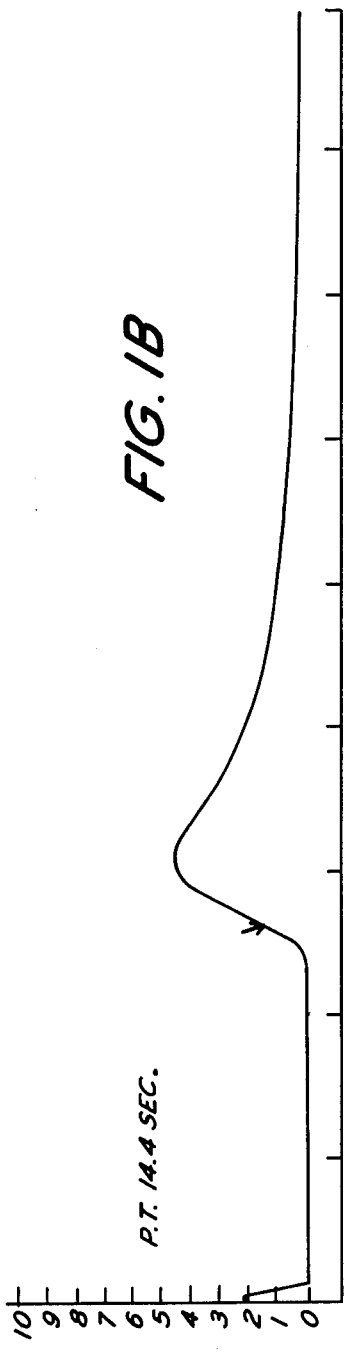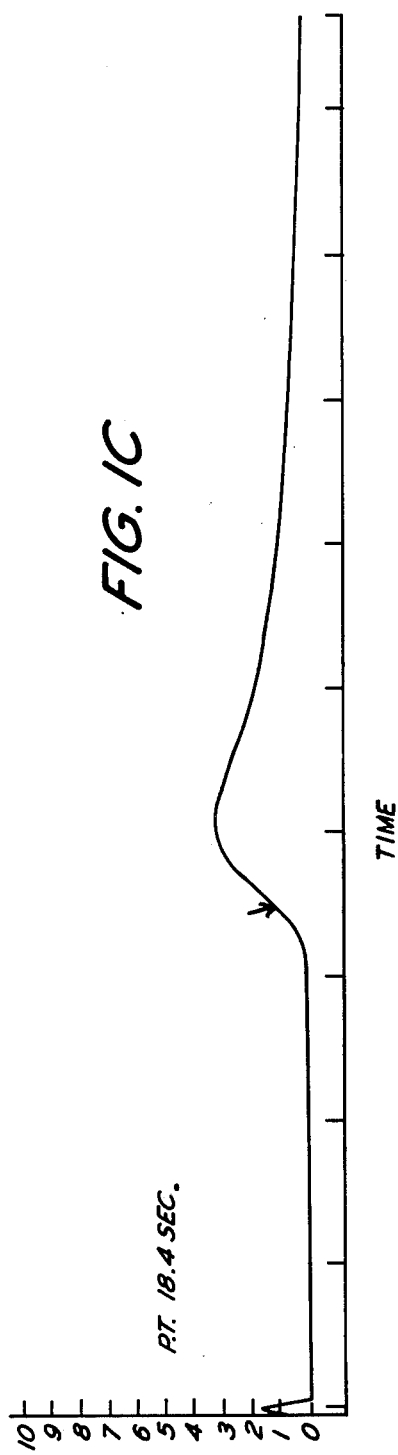
FIG. 1A, FIG. 1B, FIG. 1C: Graphs plotting the first differential of the optical density v. time curve (dO.D./dt) of a PT test.

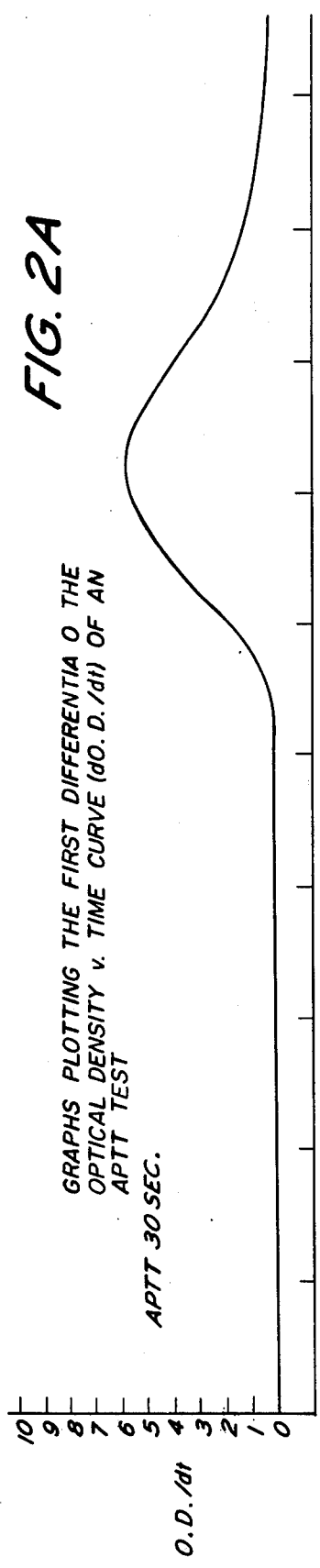
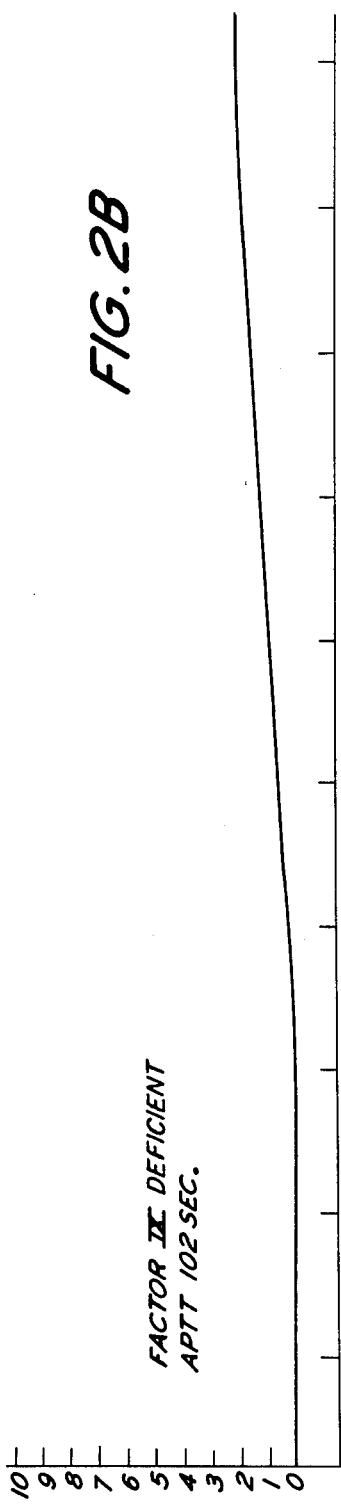
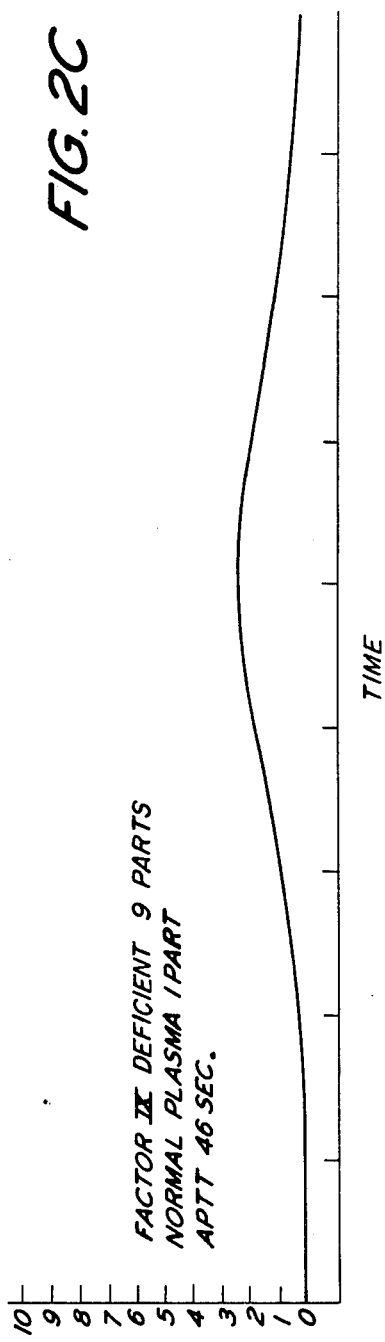

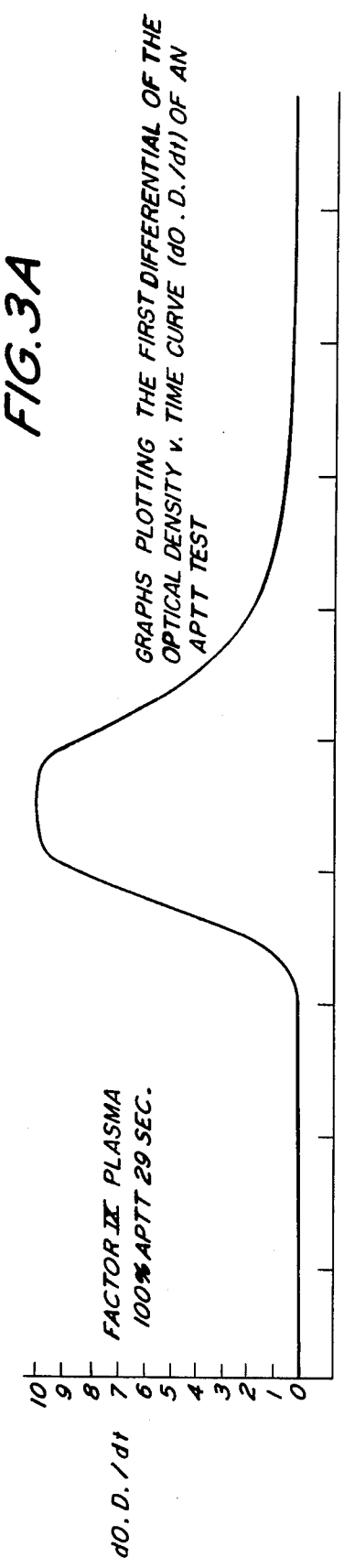
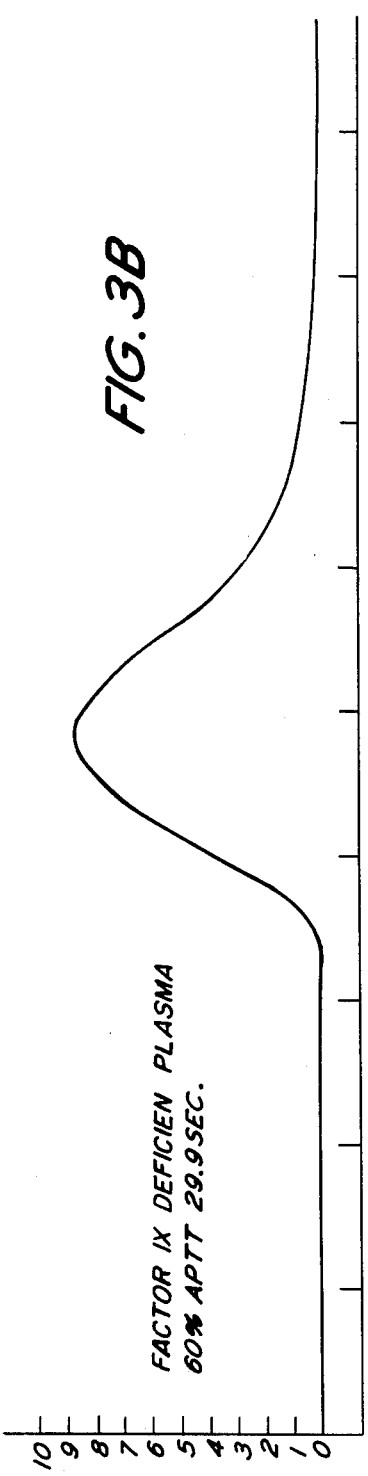
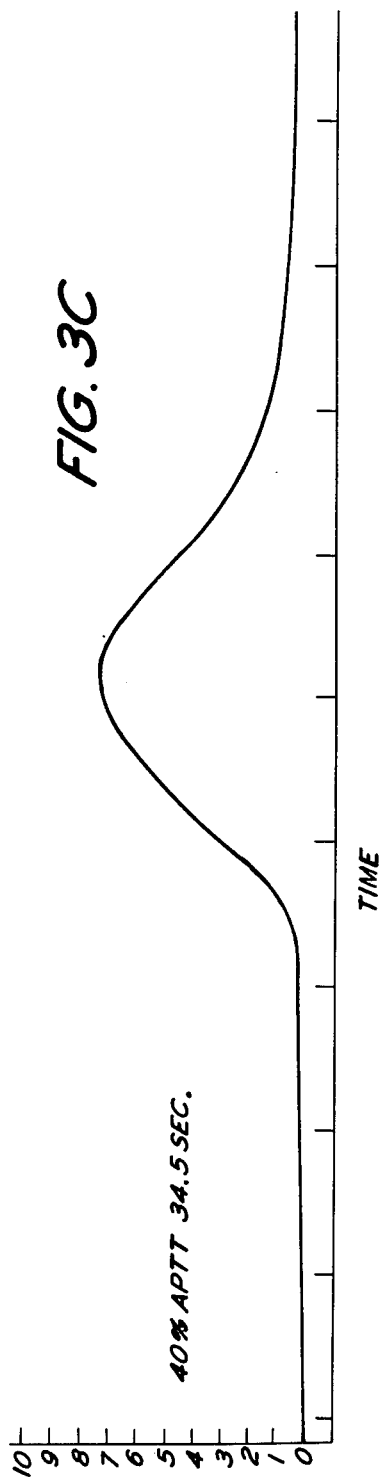

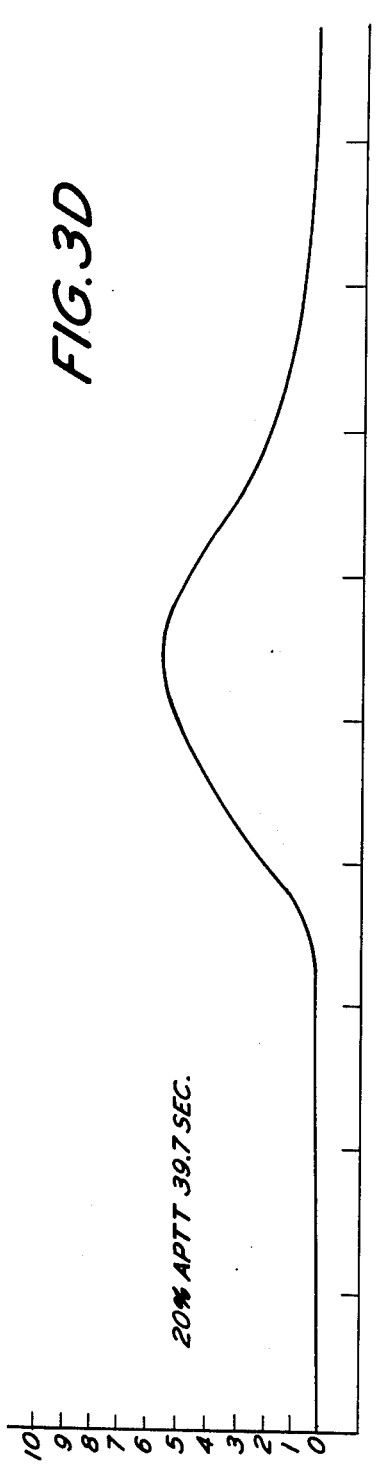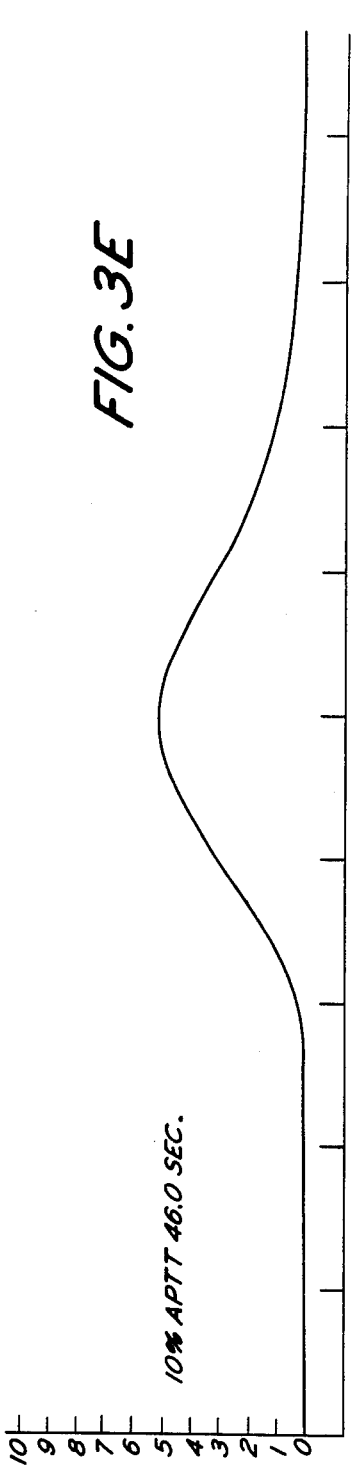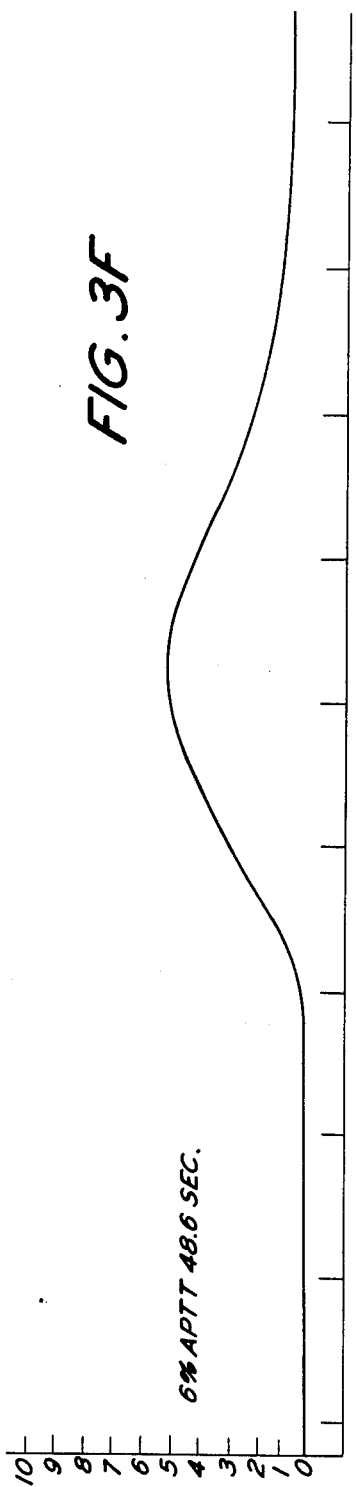

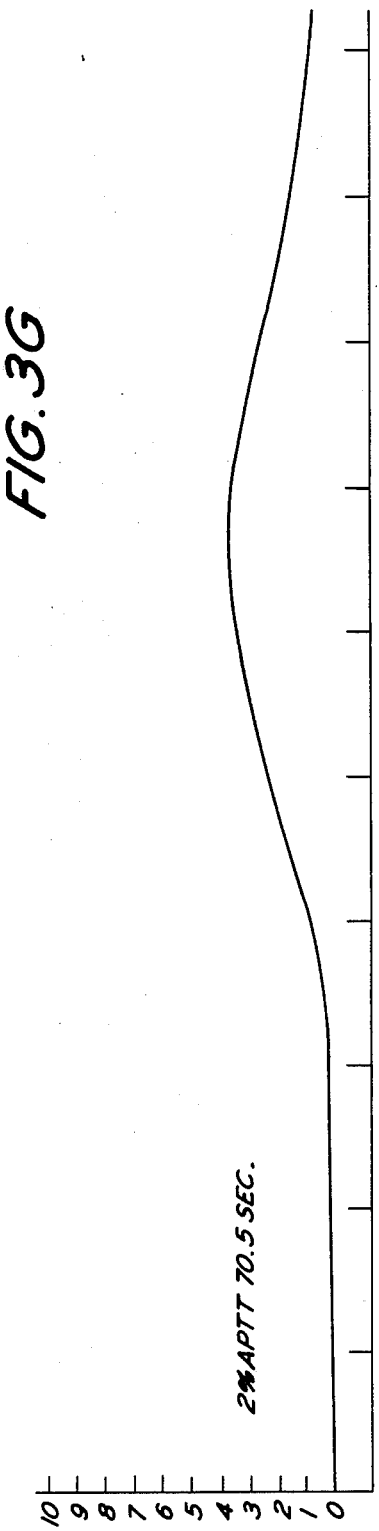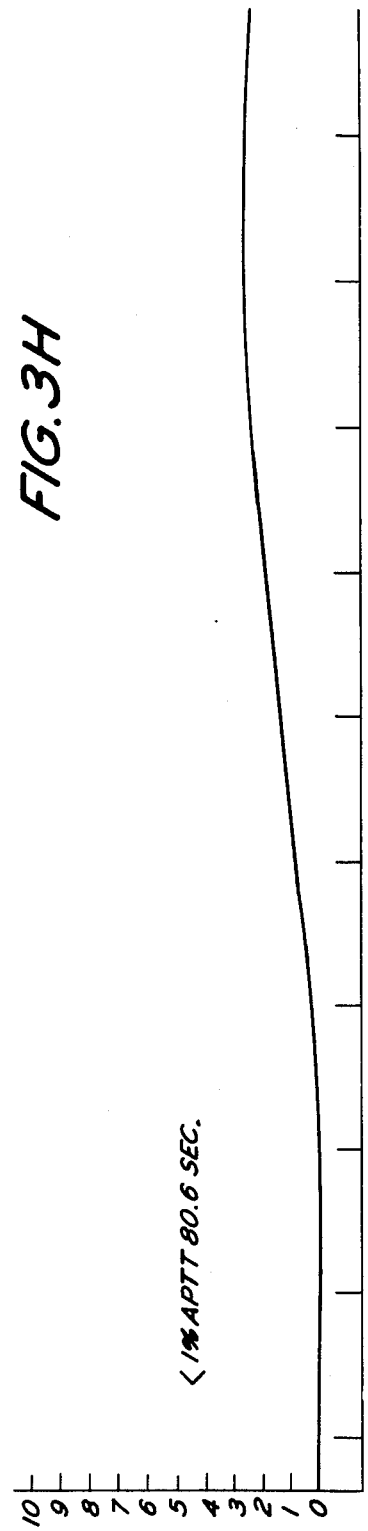

LOG-LOG PLOT OF THE PEAK VALUES OF THE CURVES SHOWN IN FIG. 3

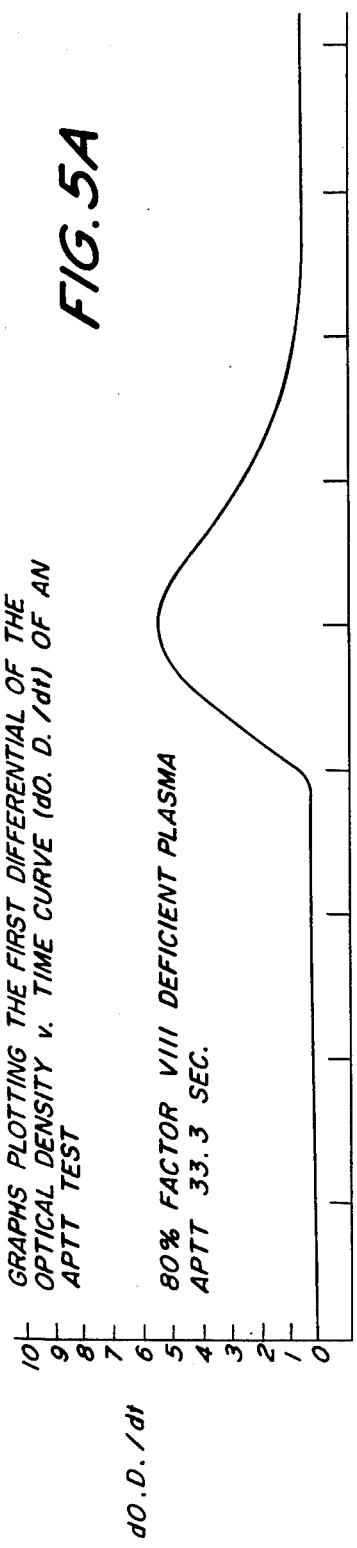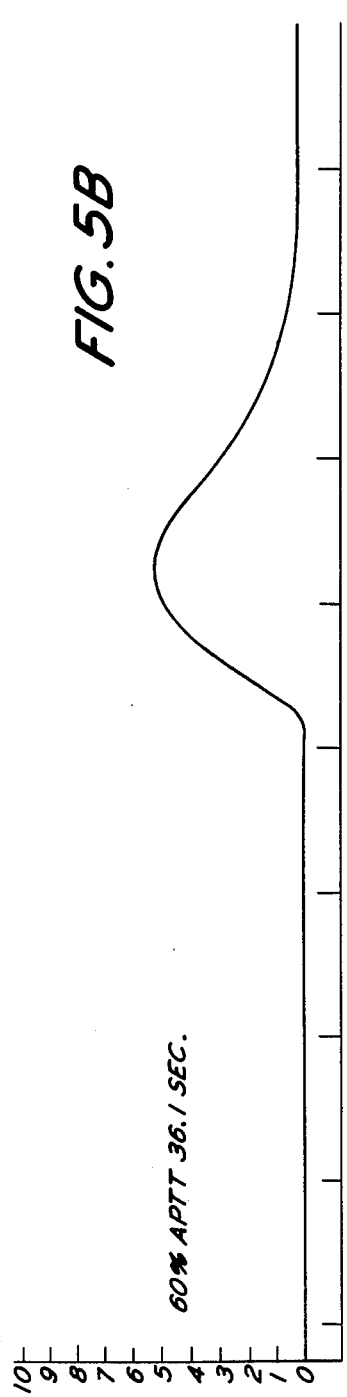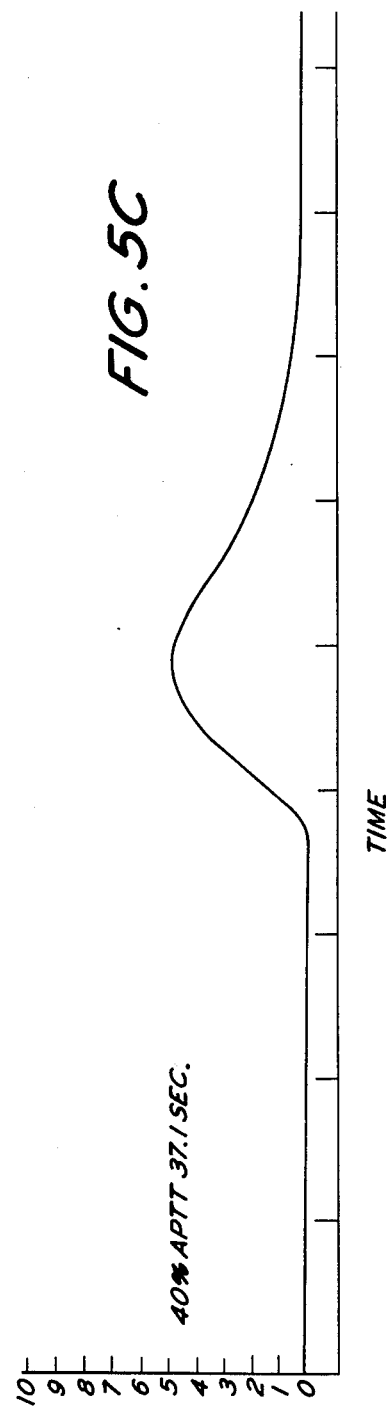
FIG.5A — GRAPHS PLOTTING THE FIRST DIFFERENTIAL OF THE OPTICAL DENSITY v. TIME CURVE (dO.D./dt) OF AN APTT TEST
80% FACTOR VIII DEFICIENT PLASMA APTT 33.3 SEC.
FIG.5B — 60% APTT 36.1 SEC.
FIG.5C — 40% APTT 37.1 SEC.

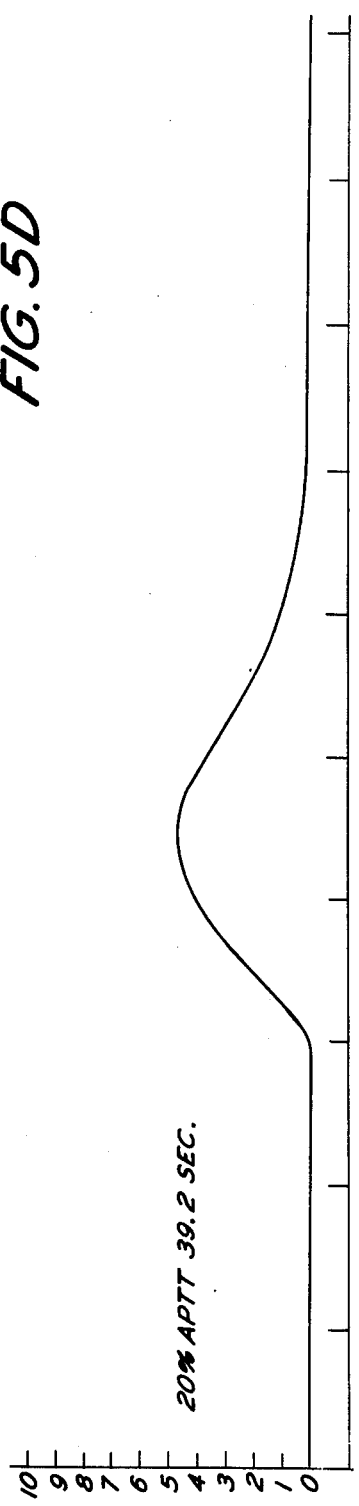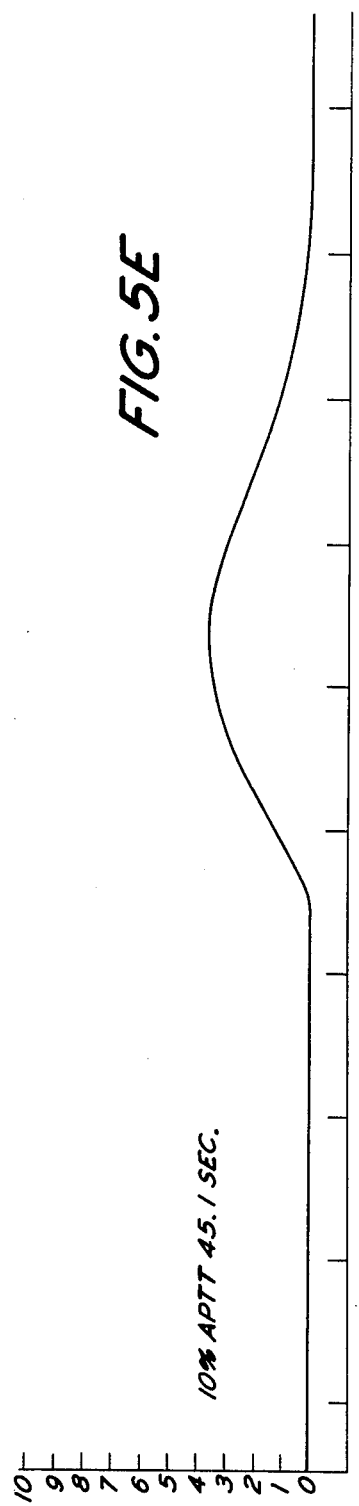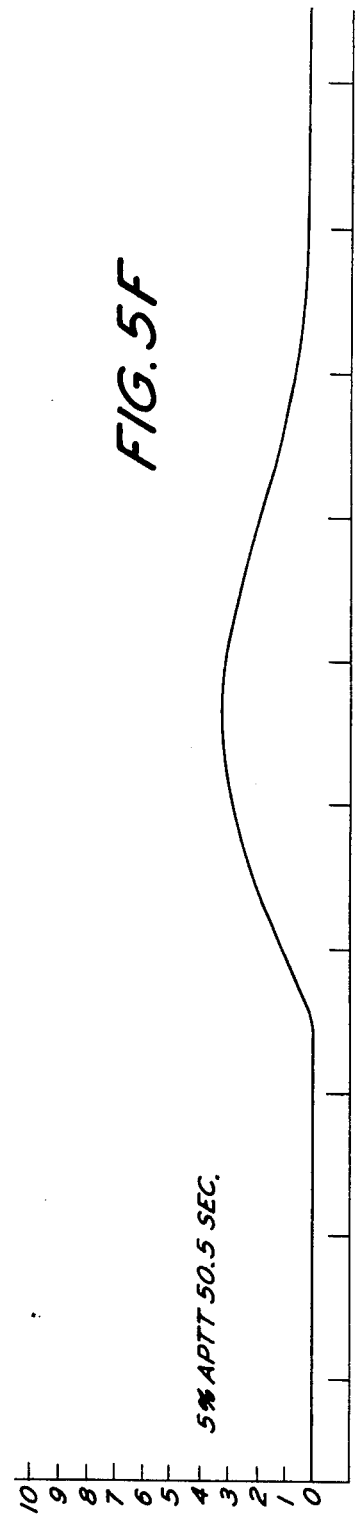

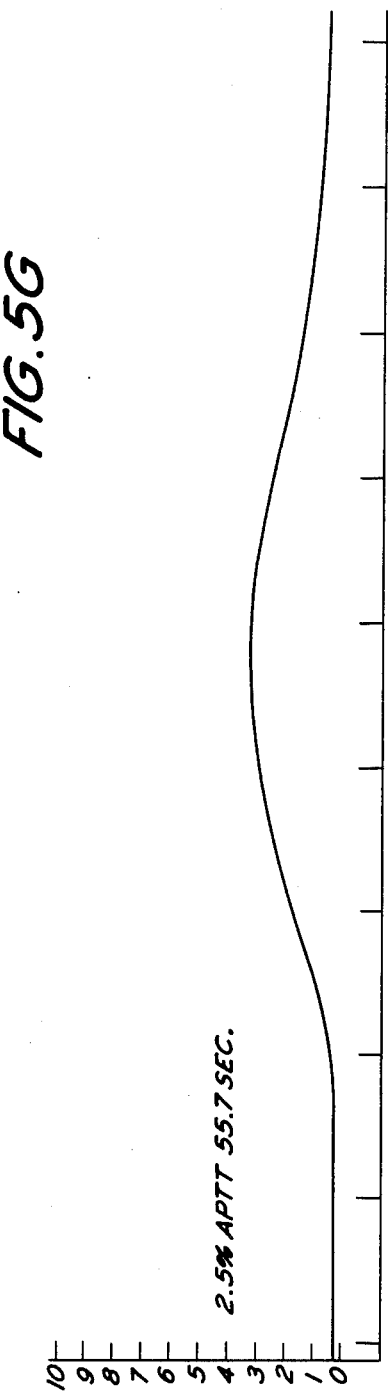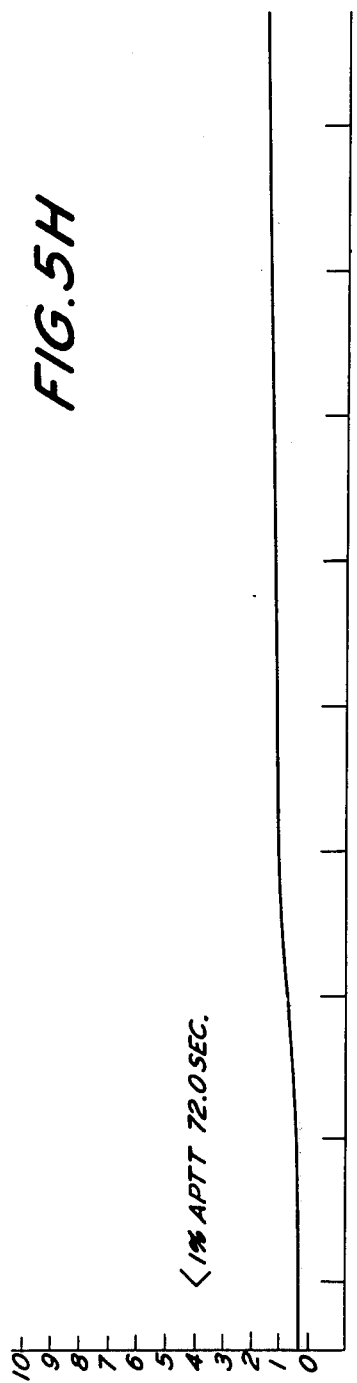

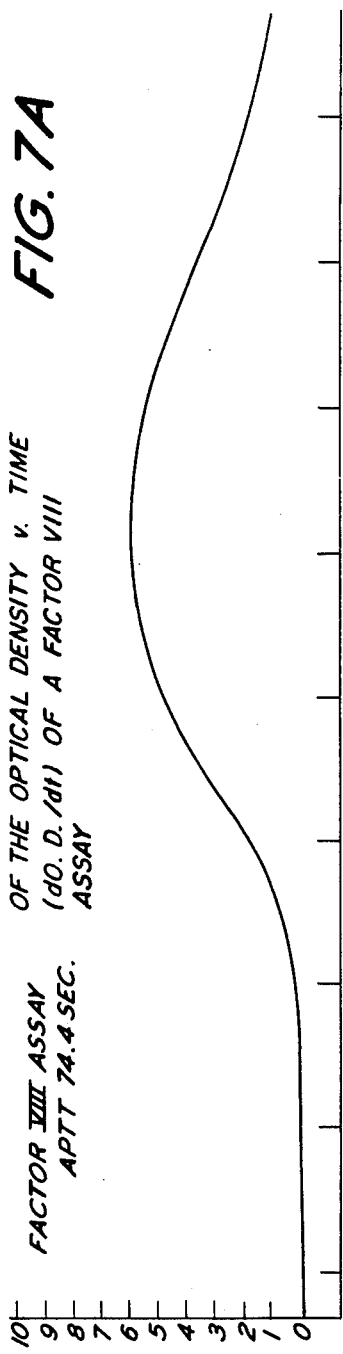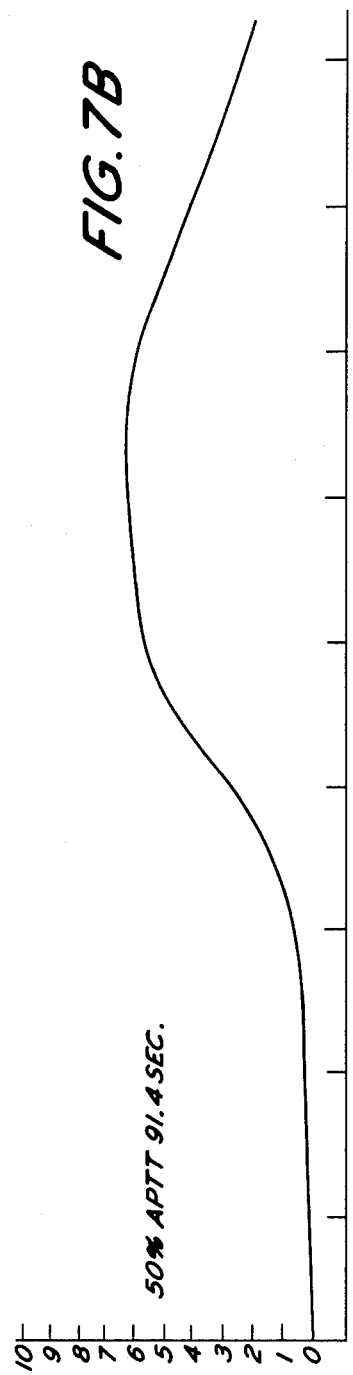

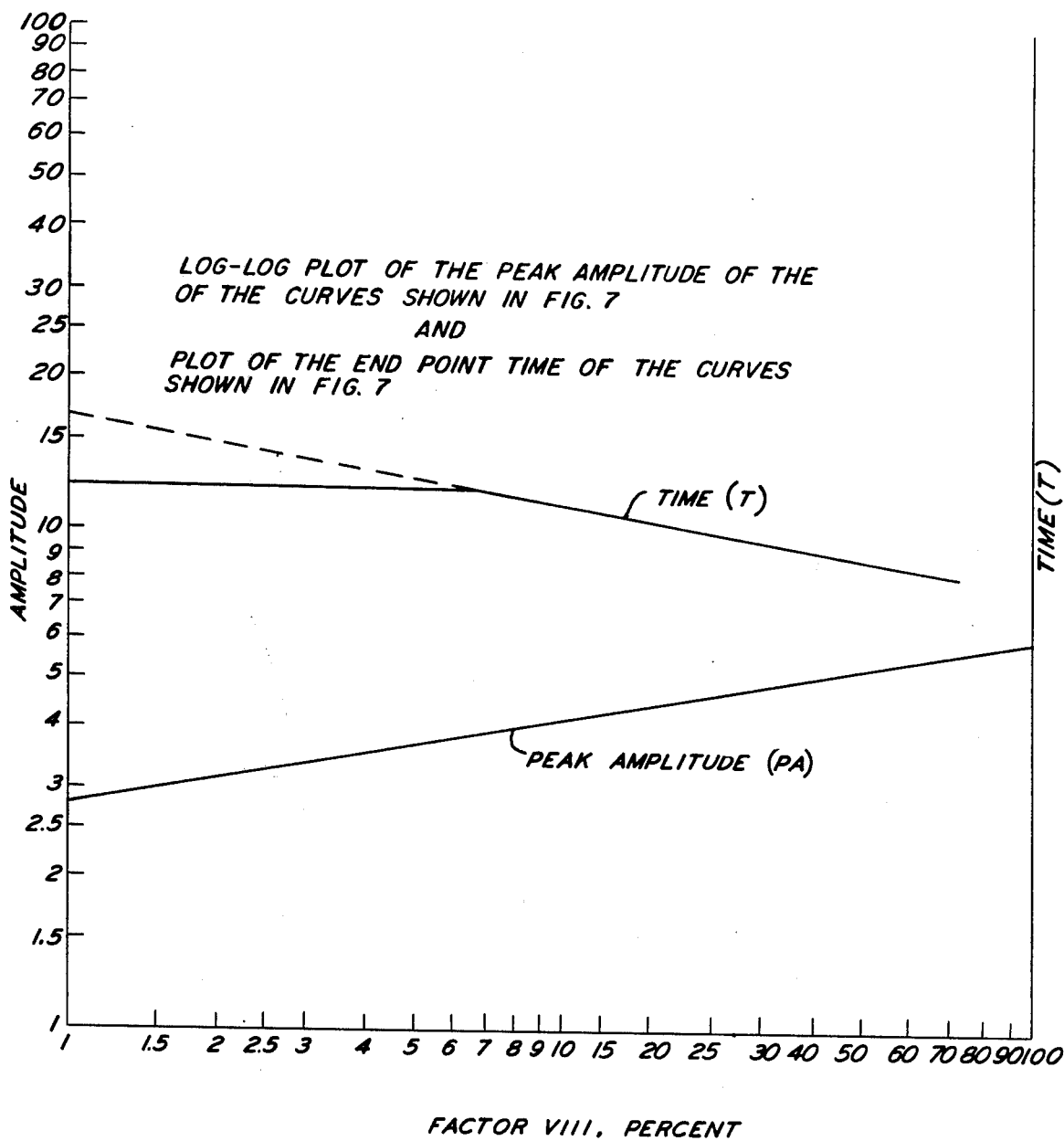

METHOD AND APPARATUS FOR DETERMINING DEFICIENCIES IN ENZYMATIC REACTORS PARTICULARLY CLOTTING FACTOR LEVELS IN BLOOD PLASMAS

This application is a continuation-in-part of application Ser. No. 411,994 filed Nov. 1, 1973, now abandoned.

This invention relates to a method and apparatus for determining blood plasma clotting factor levels including fibrinogen quantitation. More particularly, the present invention relates to a method and apparatus for directly reading particular clotting factor levels in percent activity or fibrinogen in weight percent.

The prothrombin time test (P.T. test) and the activated partial thromboplastin time test (A.P.T.T. test) are each commonly used clinical tests to determine a patient's ability to form clots. These and other tests are extensively used by hospitals, clinics, and laboratories for preoperative evaluations and for anti-coagulant therapy administered to cardiac patients, among other patients. These tests are each based upon time and for the most part measure what is called an end point or clotting time, which occurs when fibrinogen is being polymerized to fibrin. By way of example, the "normal" range for an A.P.T.T. end point is approximately 28 to 40 seconds and the normal range for a P.T. end point is approximately 11 to 13 seconds. This normal range can vary depending upon the reagents used. All times are measured from when the last reagent or chemical is added to the plasma solution until some point during the formation of the fibrin from fibrinogen. The exact end point will depend on the particular instrument utilized; however, the preferred end point is the incipiency of fibrin formation as per U.S. Pat. No. 3,658,480.

A number of instruments have been developed for automatically measured the end point time. Among these is the instrument described in U.S. Pat. No. 3,658,480. This apparatus generates a signal which corresponds to the value of the first differential of the optical density as a function of time as it crosses a preset threshold to detect the incipiency of fibrin formation. U.S. Pat. No. 3,307,392 describes an automatic prothrombin timing apparatus which also measure the first differential of optical density of a blood plasma as a function of time. In U.S. Pat. No. 3,458,287, the second differential of the optical density as a function of time is taken to determine when the first differential changes sign thereby indicating that it has reached a peak value. While each of these patents describes an instrument which measures time, each functions in a different manner. The apparatus described in U.S. Pat. No. 3,658,480 does not look for a peak value, such as in U.S. Pat. No. 3,458,287. Rather, it looks for the point where the first differential signal exceeds a predetermined value less than the peak value. The important point is that the tests and hence these instruments and others all measure time to determine the ability of a patient's blood to form a clot.

As part of the present invention, it has been determined that time alone is not an accurate method for determining the ability of a patient's blood to form a clot especially under traumatic conditions such as injury, shock or surgery. Nor is time alone sufficient for making accurate determinations of factor percent activity or fibrinogen levels in a patient's blood plasma. The present invention provides a new and unobvious method and apparatus for making these determinations.

In accordance with the present invention, these determinations are made as a function of the peak value of the first differential of the optical density-time curve of a plasma undergoing clotting. It has been found that this relationship is linear for fibrinogen and logarithmic for intrinsic factors VIII, IX, XI and XII as well as extrinsic factors II, V, VII and X, and it can be reproduced.

The process of blood coagulation is extremely complex. In general, it involves the generation of fibrin fibers formed by the polymerization of molecules of protein called fibrinogen. It is known that prothrombin converts to thrombin, and when enough thrombin has formed, it catalyzes the fibrinogen into fibrin. Some authorities treat the formation of fibrin in a step-like or cascade fashion. For convenience, the process is divided into three interdependent phases. In phase I, a substance known as thromboplastin is formed by the sequential action of certain blood factors (V, VIII, IX, X, XI and XII) with platelet lipid in the presence of calcium (the intrinsic system) or by the action of factor VII on tissue thromboplastin (factor III). In phase II, the thromboplastin, in the presence of blood factors V, VII and X and calcium, helps to convert prothrombin (factor II) into active form, thrombin. In phase III, the thrombin enzymatically aids in the polymerization of fibrinogen to produce fibrin which forms the substance of the clot.

It should be noted that the present invention deals entirely with thrombin clottable fibrinogen. There may be known types of fibrinogen which are not clottable by thrombin. These, however, are not considered in this invention.

The International Committee on Blood Clotting recognizes eleven clotting factors (I–V and VII–XII) as being involved in the clotting process, most of which are enzymatic in nature. A new factor (factor XIII) has been uncovered and is now also recognized. It is believed that fibrin is stabilized by factor XIII. Abnormal blood coagulation may result from either quantitative or qualitative congenital defects of the ten plasma factors participating in the process, and from any acquired disease involving these factors or from administration of anti-coagulant drugs. For example, it is known that classical hemophilia results from a factor VII deficiency. The absence of factor IX produces a hemophilioid type defect (hemophilia B-Christmas Disease).

A closer examination of the various tests such as the P.T. test and the A.P.T.T. test has shown that the measurement of time to determine the existence and relative activity level of a plasma clotting factor is at best a gross test. Certainly time, if prolonged, may merely indicate the existence of an abnormal factor level (or levels) without showing which factor. But the measurement of time until the appearance of an end point may not necessarily show the depression of a plasma factor level, particularly if the time is in the "normal" range. Time figures are not absolute. "Standard" times or "ranges" vary from laboratory to laboratory, technique to technique and reagent to reagent. In one of the examples described hereinafter, an A.P.T.T. test shows an end point time of 39.7 seconds for a plasma in which factor IX has only a 20% activity level. A patient may bleed in surgery with a factor activity level of 20%. Yet, many laboratories consider an A.P.T.T. time of 40 seconds to be normal.

Clearly then, as valuable and as effective as the existing clotting time tests may be, they are of no value unless the factor level is such as to extend the end point time beyond a normal range. Unfortunately, plasma clotting factor deficiencies may exist even though end point clotting times are in the normal range, and such deficiencies can result in serious problems during surgery and other traumatic events as previously described.

The present invention overcomes this inadequacy of existing laboratory techniques for doing factor assays by providing a novel method and apparatus for determining plasma clotting factor levels. The amplitude of the first differential of the optical density-time curve is measured. It has been determined that a particular factor activity level (except fibrinogen) is a logarithmic function of the peak value (amplitude) of the first differential of the optical density-time curve. Additionally, it has been determined that fibrinogen is a linear function of the aforesaid peak value when doing the thrombin time test to quantitate fribrinogen. Accordingly, the first differential peak value of an unknown blood plasma is related to peak values as determined from a standard plasma to establish a percent activity level for a particular factor. For factor I (fibrinogen) the invention provides a read-out directly in weight per unit volume. In accordance with the present invention, the process is done automatically and independent of time without the necessity of plotting graphs. Thus, the present invention provides a new and unobvious method and apparatus for screening blood plasma for clotting factor levels. The present invention also provides a new and unobvious method and apparatus for differential detection of plasma clotting factor deficiencies.

For the purpose of illustrating the invention, there are shown in the drawings forms which are presently preferred; it being understood, however, that this invention is not limited to the precise arrangements and instrumentalities shown.

FIGS. 1A, 1B and 1C are graphs plotting against time the first differential of the optical density-time curve of a P.T. test.

FIGS. 2A, 2B and 2C are graphs plotting against time the first differential of the optical density-time curve for an A.P.T.T. test.

FIGS. 3A through 3H are graphs plotting against time the first differential of an optical density-time curve for an A.P.T.T. test done as the basis for a factor IX assay on a plasma containing 100%, 60%, 40%, 20%, 10%, 6%, 2% and <1% factor IX.

FIGS. 5A through 5H are graphs plotting the first differential of the optical density-time curve of an A.P.T.T. test done as the basis for a factor VIII assay on a plasma containing 80%, 60%, 40%, 20%, 10%, 5%, 2.5% and <1% factor VIII.

FIGS. 7A through 7H are graphs plotting against time the first differential of the optical density-time curve of a factor VIII assay.

FIG. 8 is a plot of the peak amplitude of the curves from FIGS. 7A through 7H on a log log scale and a plot of the end point or clotting time from the same curves.

Figure 4:
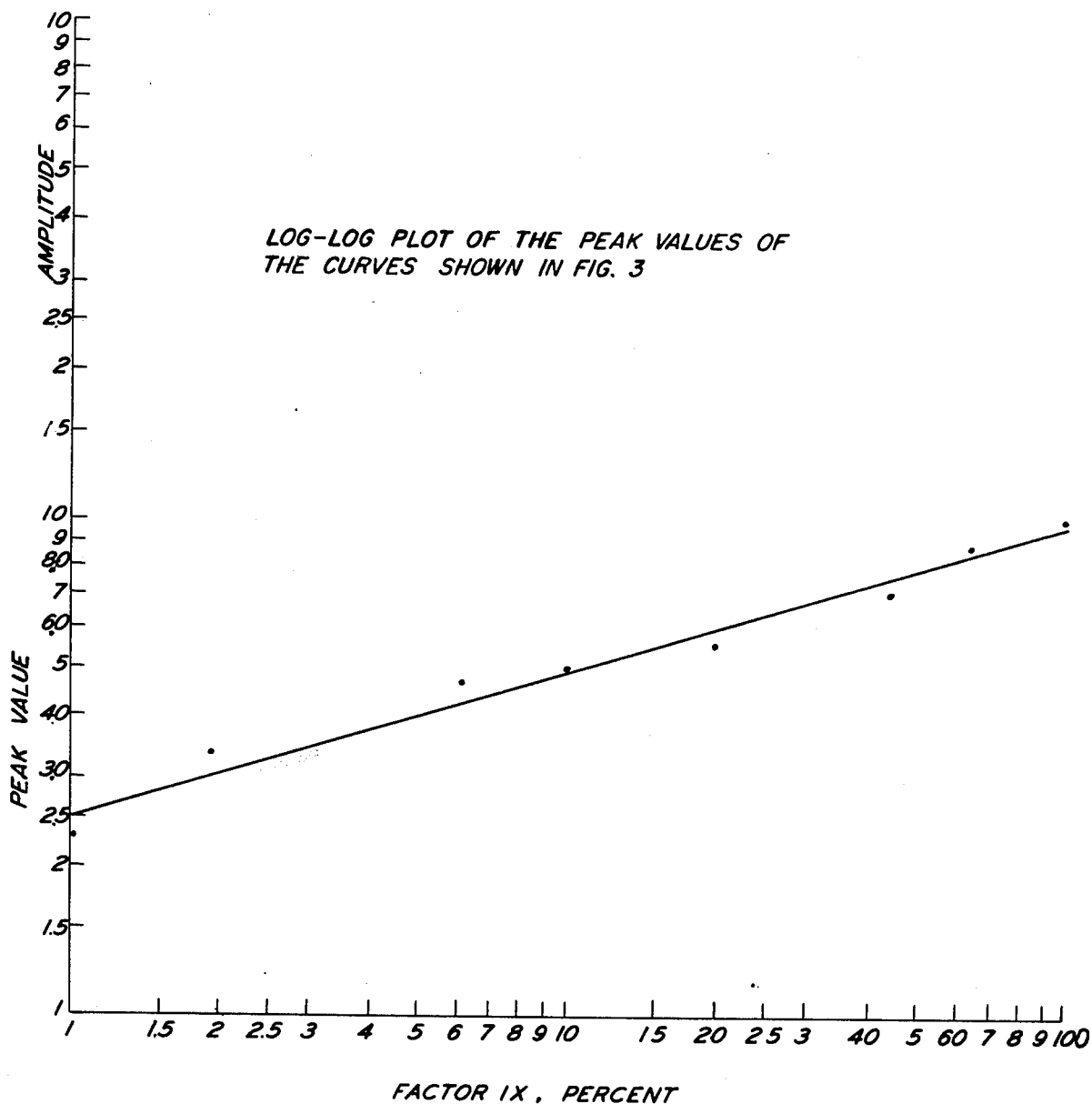
FIG. 4 is a plot of the peak values of the curves shown in FIG. 3 on a log log scale.

Most determinations of abnormalities in the ability of blood to clot are made by testing blood plasma. If a sample of blood is removed from a patient, put in a test tube and allowed to clot, the liquid portion which remains after clotting has occurred is called serum. If, prior to clotting, there is added to the whole blood an anti-coagulant reagent and if thereafter the anti-coagulated whole blood is centrifuged, the liquid portion which remains is known as plasma. Examples of anti-coagulants which are commonly used are sodium citrate and sodium oxalate. Sodium citrate is preferred for the purpose of this invention because it provides a smoother first differential signal, but the invention is not so limited and it will function with either anti-coagulant. Normally, the anti-coagulants are added to the blood in the ratio of one part anti-coagulant and nine parts whole blood.

The present invention relates to a method and apparatus for measuring plasma clotting factor levels. Reference herein will most often be made to dificiencies in plasma clotting factor levels since that is the usual case. However, instances of elevated clotting factor levels have been detected, such as factor VIII in some thrombotic patients. The present invention is quite capable of detecting such elevated levels and hence is not limited to the measurement of deficiencies alone even though the measurement of deficient levels is most often mentioned.

The prothrombin time test (P.T.) and the activated partial thromboplastin time test (A.P.T.T.) have already been mentioned. There are other types of tests such as the thromboplastin generation test (T.G.T.) and thrombin test (T.T.) which are used to determine platelet and plasma factor deficiencies and quantitative fibrinogen, respectively. Still another test is the prothrombin and proconvertin test (P&P). These other tests need not be described in detail as they are well known to those skilled in the art. However, a brief description of the P.T. test and the A.P.T.T. test may be of assistance in understanding the present invention. The prothrombin time test (P.T) is performed by obtaining 0.1 milliliter of anit-coagulated blood plasma and adding to it 0.1 milliliter of thromboplastin and 0.1 milliliter of calcium chloride. The clotting or end point time is measured from the time of the addition of the thromboplastin and calcium chloride until the incipiency of a clot. The test is performed with the mixture at 37° C. which is body temperature.

The P.T. test is sensitive to factors I, II, V, VII and X; that is, a deficiency in these factors may result in an extension of the clotting time beyond the normal range. The normal range for a P.T. test is approximately 11 to 13 seconds. The normal range can vary depending upon the reagent used; but these deviations are standardized in existing manuals.

An activated partial thromboplastin time test (A.P.T.T.) is performed by adding 0.1 milliliter of cephalin reagent to 0.1 milliliter of plasma. The plasma and cephalin are incubated together from between 2 to 5 minutes depending upon which brand of the cephalin reagent is utilized. Thereafter, 0.1 milliliter of calcium chloride is added to the incubated mixture and the end point is measured from the time of introduction of the calcium chloride. The calcium chloride has a molarity of 0.02 –0.03 moles. The normal time range for an A.P.T.T. test is approximately 28 to 40 seconds, again depending upon the brand of the reagent. An A.P.T.T. test is sensitive to deficiencies in blood factors I, II, V, VIII, IX, X, XI and XII.

These various tests (e.g., P.T. and A.P.T.T.) are often used in conjunction to isolate groups of possible factor dificiencies. For example, if a P.T. test falls within the normal range but the A.P.T.T. test shows an abnormally long clotting time, then by deduction it is known that one of factors VIII, IX, XI or XII is probably the cause of the abnormal clotting time. According to known laboratory procedures, other tests are then induced to determine which of these four factors may be causing the abnormal clotting time. Other tests available to the clinician are factor assays for each and every one of the factors known to exist. Factor assays are not done at the outset because they are long, tedious, subject to error and they are easily invalidated.

There are several methods of measuring end point times. These include mechanical, manual, indirect optical and optical density procedures. Almost all tests of blood clotting are done by measuring from the time the last reagent is added to some point during the formation of the fibrin end point. The formation of fibrin is detectable by changes in optical density because it is insoluble in the plasma solution and therefore forms a precipitate.

As previously indicated, the precursor (or catalyst) of the process for forming fibrin from fibrinogen polymerization is thrombin. The incipiency of the formation of a clot, that is the formation of fibrin, is determined by a change in the slope of the optical density-time curve. Existing apparatus measure the first differential of the optical density curve to determine end points. An example of such apparatus is disclosed in U.S. Pat. Nos. 3,307,392 and 3,658,480.

The present invention is concerned with an evaluation of the significance of the first differential of the optical density-time curve. It has been found that the peak value of the first differential of the optical density-time signal is significantly related to one or more clotting factor deficiencies. As previously, stated, the precursor (or catalyst) of fibrinogen polymerization is thrombin. Basically, clotting factor deficiencies result in a difference in the rate of generation of thrombin and the amount of thrombin that is generated. Stated otherwise, the rate of formation of thrombin and the amount of thrombin formed depend upon the clotting factors and the way of factors react with each other and upon each other. It has been found that the presence, absence or partial absence of normal clotting factors and the way they react with each other is reflected in the slope of the peak value of a graphical plot of the first differential of the optical density time curve of a blood plasma undergoing clotting [P.T. or A.P.T.T. or T.T. thrombin time (fibrinogen-factor I)] as a function of time.

If the output of the apparatus described in U.S. Pat. No. 3,658,480 be graphically plotted for a P.T. test, then the result may be similar to the graphs illustrated in FIGS. 1A, 1B and 1C. The apparatus described in that patent measures the incipiency of the formation of a clot on the upward slope of the first differential curve as indicated by the arrows in the graphs shown in FIGS. 1A, 1B and 1C. FIG. 1A shows a first differential curve for normal blood plasma having a clotting time of 11.5 seconds in a P.T. test. The curve of FIG. 1B shows a clotting time of 14.4 seconds for a P.T. test. The curve of FIG. 1C shows a blood clotting time of 18.4 seconds for a P.T. test. FIGS. 1B and 1C represent curves for blood plasma having different levels of factors II, VII and X.

It has been determined that the formation of a clot is much more complicated than originally believed. The curve illustrated in FIG. 1A is for normal blood. The graph in FIG. 1B is known to be abnormal. Its P.T. clotting time is 14.4. seconds, the peak height is lower than the curve illustrated in FIG. 1A and the shape of the descending slope is significantly different. This difference is even more noticeable in FIG. 1C (clotting time 18.4 seconds) which has a much lower peak value and a radically different descending slope. Thus, it is clear that the characteristic shape of the curves in FIGS. 1B and 1C are the result of multiple factor deficiencies. In the given example, these are factors II, VII and X. Similar differences in the characteristic shape of the first differential curve could be obtained by taking other multiple or single factor deficiencies.

FIGS. 2A, 2B and 2C show the results of an A.P.T.T. test for normal blood plasma, factor IX deficient blood plasma and a mixture of factor IX deficiant and normal blood plasma, respectively. For purposes of this application, a blood plasma is considered to be wholly deficient of a particular factor if its activity level is less than 1%. The commercially available factor deficient substrate plasmas which are routinely used are not totally free of the deficient factor. They generally have between 0.1 and 0.15% of the supposedly deficient factor in them. Such a blood plasma is illustrated in FIG. 2B which has an A.P.T.T. time of 102 seconds. In FIG. 2C, nine parts of factor IX deficient plasma are mixed with one part of normal plasma. The A.P.T.T. time of the curve in FIG. 2C is reduced to 46 seconds and the shape of the curve is altered in that the peak value as well as the clotting time falls somewhere between the values shown in FIGS. 2A and 2B. Thus, the shape of the first differential curve for a plasma having a single factor deficiency also will vary as a function of the amount of that deficiency.

Referring now to FIGS. 3A through 3H, there are shown eight curves for differing mixtures of normal and factor IX deficient plasmas. These curves are all plots of the first differential of the optical density as a function of time as derived from an apparatus such as that described in U.S. Pat. No. 3,658,480. They are all A.P.T.T. tests.

FIG. 3A shows normal blood plasma; that is, plasma with factor IX at a 100% activity level. FIG. 3B shows plasma with factor IX at a 60% activity level. FIG. 3C shows plasma with factor IX at a 40% activity level. FIG. 3D shows plasma with factor IX at a 20% activity level. FIG. 3E shows the plasma with factor IX at a 10% activity level. FIG. 3G shows a 2% activity level for factor IX. FIG. 3H shows a factor IX activity level of less than 1%.

As expected, the end point or clotting time becomes longer as the activity level drops. Significantly, the end point time in the curve illustrated in FIG. 3D is 39.7 seconds even though the plasma is known to have a relatively low 20% factor IX activity level. Such an end point time is considered by many laboratories to fall within the normal range for the A.P.T.T. time. Yet a patient with a factor IX activity level of 20% or below may bleed in surgery. This therefore demonstrates that end point time alone is not necessarily a sufficient or specific determinant of blood plasma factor deficiency.

Further inspection of FIGS. 3A through 3H that the peak amplitudes of the first differential curve drops as the activity level becomes lower. This is best illustrated in FIG. 4 where the peak amplitude of each of the curves in FIGS. 3A through 3H is plotted against the percent of activity of factor IX on log log paper. Inspection of the plot shown in FIG. 4 shows that it is approximately a straight line. Indeed, allowing for variables normally encountered in testing, it can be concluded that it is indeed a straight line.

FIGS. 5A through 5H and FIG. 6 are similar to the graphs illustrated in FIGS. 3 and 4 but for mixtures of normal and factor VIII deficient plasmas. All graphs are for an A.P.T.T. test.

FIG. 5A shows an 80% factor VIII activity level with an end point time of 33.3 seconds. FIG. 5B shows a 60% factor VIII activity level with an end point time of 36.1 seconds. FIG. 5C shows a 40% factor VIII activity level with an end point time of 37.1 seconds. FIG. 5D shows a 20% factor VIII activity level with an end point time of 39.2 seconds. FIG 5E shows a 10% factor VIII activity level with an end point time of 45.1 seconds. FIG. 5F shows a 5% factor VIII activity level with an end point time of 50.5 seconds. FIG. 5G shows a 2.5% factor VIII activity level with an end point time of 55.7 seconds. FIG. 5H shows an end point time of 72 seconds for a factor VIII deficient plasma having an activity level of less than 1%.

Figure 6:
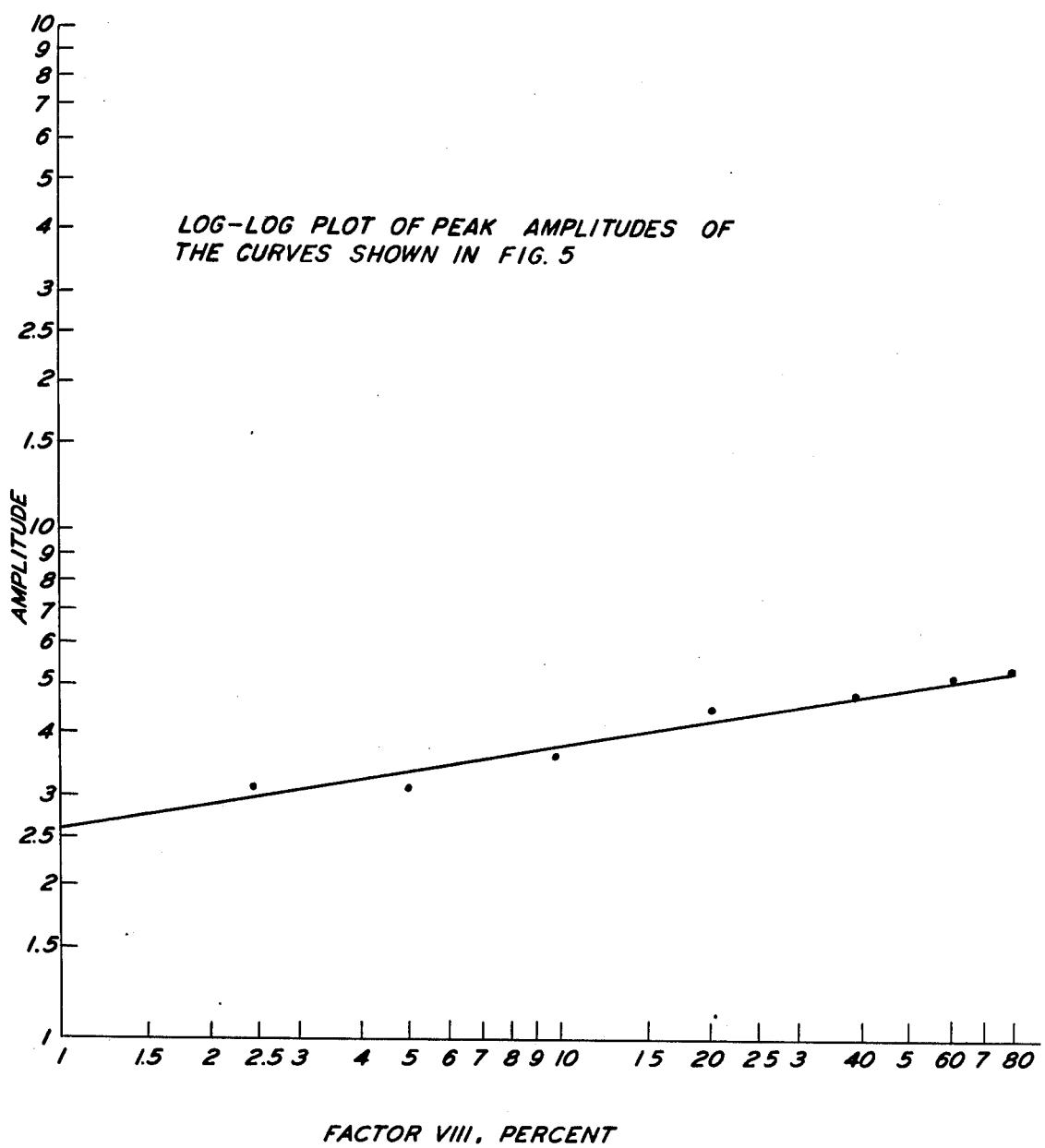
FIG. 6 is a plot of the peak amplitudes of the curves shown in FIG. 5 on a log log scale.
Figure 7D:
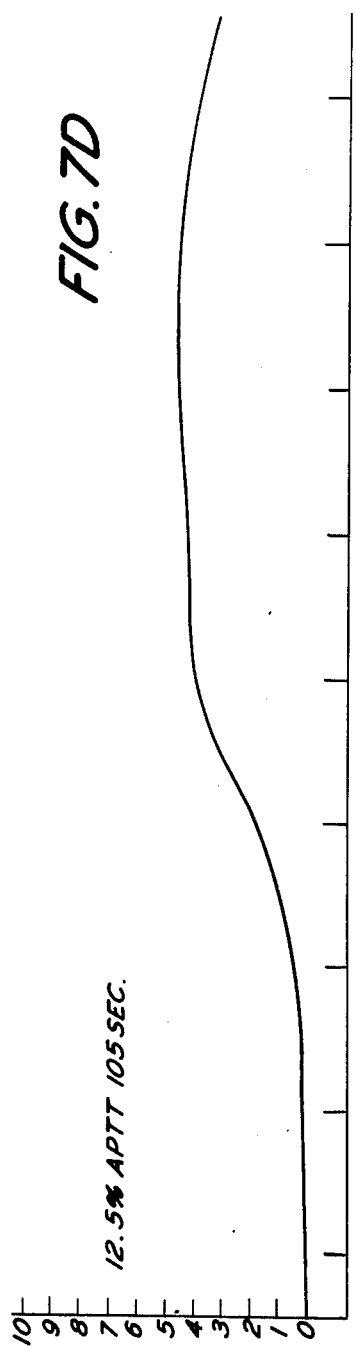
Figure 7E:
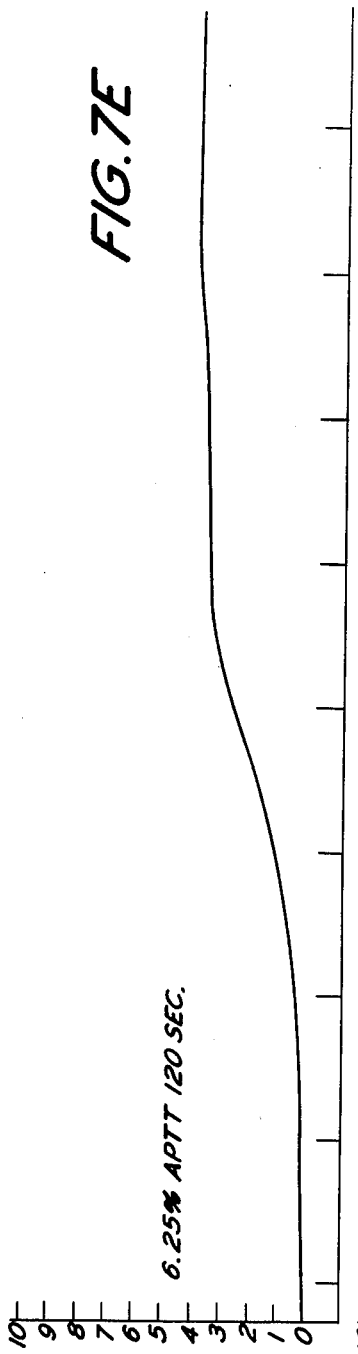
Figure 7F:
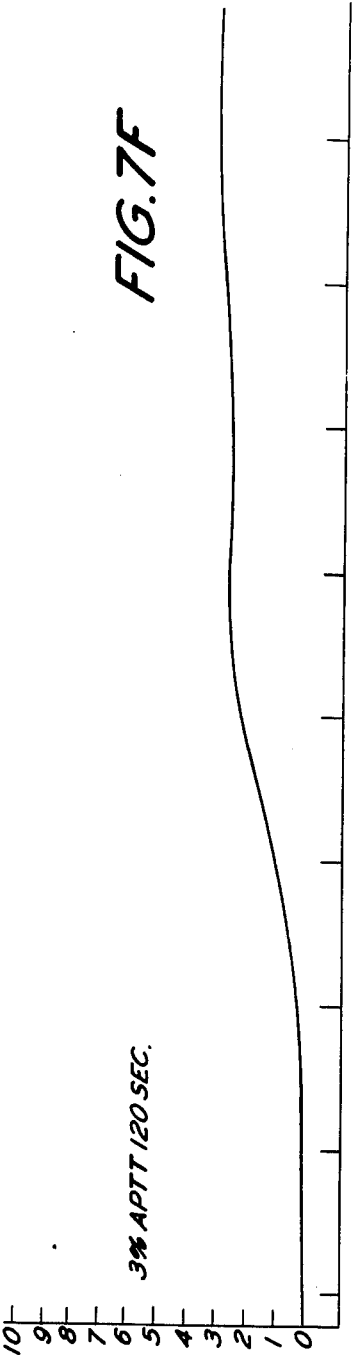
Figure 7G:
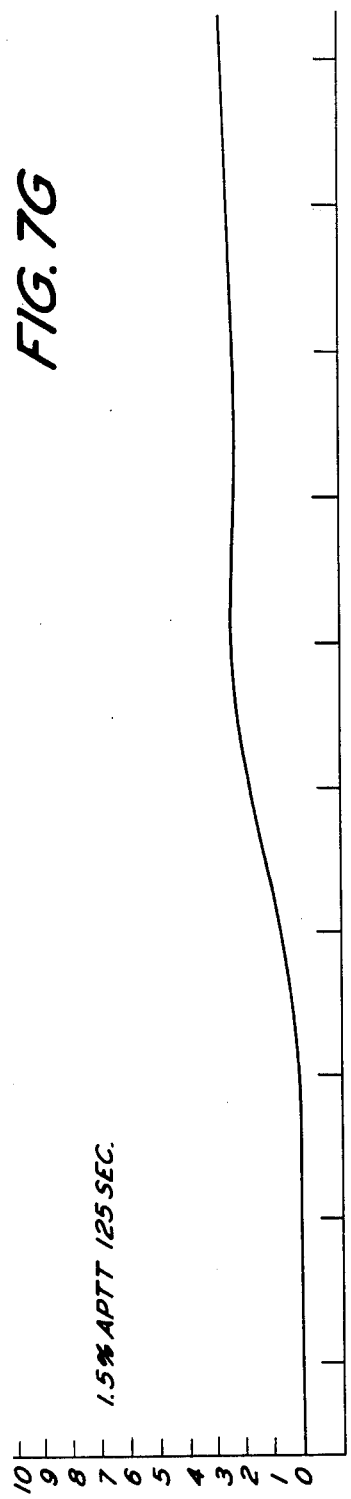
Figure 7H:
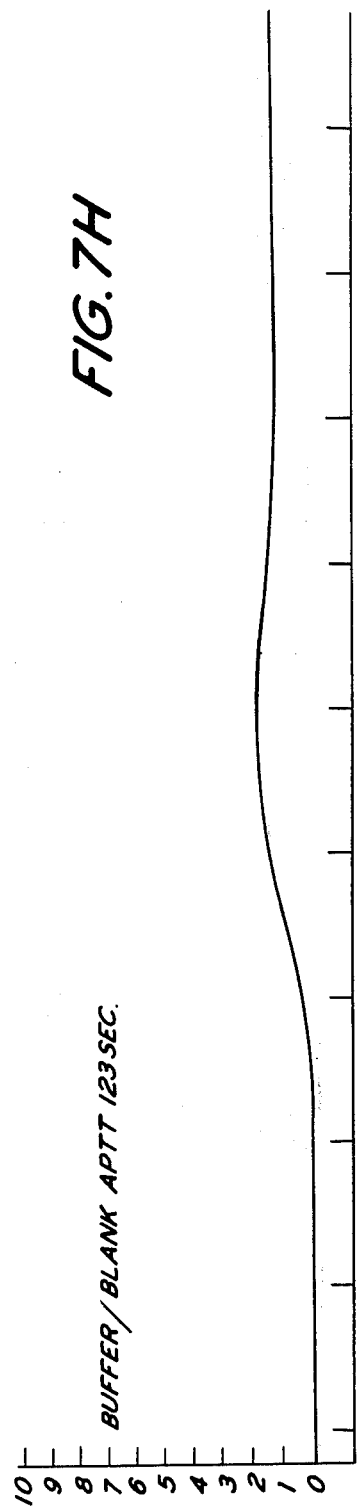

Inspection of the curves in FIGS. 5A through 5H again shows that the peak value of the first differential curve decreases along with the activity level. When this is plotted on log log paper as shown in FIG. 6, a straight line relation results as illustrated.

It should also be noted that the end point times vary by only six seconds between the 80% and 20% activity levels even though there is a significant 60% difference in the level of clotting factor. See FIGS. 5A through 5D. A patient with a 20% activity level of factor VIII is a potential bleeder and is not a safe surgical risk. Yet this patient may very well be approved for surgery based on an A.P.T.T. end point time of 39.2 seconds. Indeed, FIG. 5E shows a 10% activity level for factor VIII with an A.P.T.T. time of 45 seconds. In some laboratories, that time value is considered to be a high normal or a gray zone clotting time. Only a specific factor assay would have indicated the extend of the factor VIII deficiency. On the other hand, the presence of a factor deficiency is readily apparent by inspection of the graph in FIG. 6.

The graphs shown in FIGS. 3, 4, 5 and 6 each simulate factor deficiencies by mixing normal blood plasma with a known factor deficient plasma and then taking the A.P.T.T. time. The result is a straight line relation between the peak value of the first differential of the optical density-time and the simulated factor activity levels. FIGS. 7A through 7H represent similar first differential curves as derived by mixing factor VIII deficient plasma with diluted normal plasma as in doing a conventional factor assay. These curves are explained in detail below.

Conventionally, an assay to determine a factor deficiency is performed in the following manner. First, a plasma known to be deficient in a particular factor is added to a test tube. For example, a factor VIII deficient plasma could be used. A plasma with an A.P.T.T. time in excess of 100 seconds is considered to have an activity level which is less than 1%.

The next stop is to dilute normal plasma with a buffered saline solution at ratios of 1:10, 1:20, 1:40, 1:80, 1:16, 1:320. The 1:10 diluted normal plasma is described as having 100% activity level. The 1:20 dilution is described as 50% activity level and so forth through the 1:320 dilution. The next step is to take 0.1 milliliter of the 1:10 (100% activity) normal plasma and add it to 0.1 milliliter of a known factor VIII deficient plasma (less than 1% activity level) plus 0.1 milliliter of an A.P.T.T. reagent and 0.1 milliliter of calcium chloride, at the correct molarity. Upon the addition of the calcium chloride, the end point of clotting time is measured and this is illustrated in FIG. 7A.

The procedure is repeated for the 1:20, 1:40, 1:80, 1:160 and 1:320 dilutions of normal blood in exactly the same quantities and the times are again measured as shown in the graphs illustrated in FIGS. 7B through 7H. What these curves represent is the ability of normal diluted plasma to correct the clotting time of theknown factor deficient plasma. In the example given, the plasma is deficient in factor VIII.

The clotting or end point time is set forth in each of FIGS. 7A through 7H and need not be repeated herein. Because the normal plasma is diluted, the end point times are significantly longer than for undiluted plasma.

Inspection of the curves in FIG. 7A through 7H shows again that the peak value is directly related to percent activity. This is plotted in FIG. 8 which shows that there is a straight line relationship between the peak value of the first differential of the optical density-time and the percent activity level.

The foregoing procedure was done for a known factor deficient plasma. The next step is to dilute the patient's plasma having an unknown factor deficiency level as above. For example, a 1:10 dilution and 1:20 dilution can be made. Using the same reagent, the A.P.T.T. end point time and peak amplitude for these two dilutions are determined. By finding where the peak value falls on the curve of FIG. 8, the percent activity is thereby known.

To illustrate the advantage of using peak values rather than end point times, the time curve marked T has been plotted in FIG. 8. This curve shows the relationship between clotting time in seconds and percent level. Note that FIG. 7E through 7H show no significant difference in clotting time even though it is known that the percent activity level is much lower in each curve. This is graphically illustrated in FIG. 8 by the level portion of the curve T. The reason for the level portion of the curve is because the clotting time procedure loses sensitivity somewhere between approximately 1 and 6% activity; i.e., time no longer increases as a function of dilution. The dotted line portion of the curve (T) shows what the results should be if time alone is to be relied upon by extrapolation. A valid and scientifically correct extrapolation of the time line is not possible, however, since no meaningful method exists to determine and verify the time line values below approximately 6%. This demonstrates that the existing assay tests for determining factor activity levels are not sensitive below approximately a 6% activity level. This is significant because a hemophiliac may not bleed if his activity level is above 6%. It therefore is important and essential to know the hemophiliac's percent activity level in the range below 6%. However, this cannot be known if reliance is placed on clotting time along. In accordance with the present invention, it can be readily determined by measuring the peak amplitude of the first differential of the optical density-time curve. Thus, the present invention provides a method for extending the reliability of factor assays.

Thus far, the discovered relationship between the peak value of the first differential of the optical density-time curve and percent activity has been stated in terms of graphical illustrations plotted on log log paper. These have all been shown to be a straight line relationship. On linear paper, it would be exponential.

This relationship can be stated in mathematical terms as follows:

Percent activity (X) for a factor deficient plasma is a logarithmic function of the peak amplitude (Y) of the first differential of the optical density as a function of time:

$$\log X = N \log Y - C \text{ or} \qquad (1)$$

$$X = Y^N - C$$

where:
N is the slope of the illustrative curve
C is a constant to account for deviations from zero (i.e., an offset factor).

The foregoing clearly establishes the relationship between the peak amplitude of the first differential of the optical density-time curve and the quantum of factor deficiency as a function of percent activity level. Having determined that there is a relationship, it is now possible to use such relationship to determine plasma factor deficiencies electronically.

Figure 9:
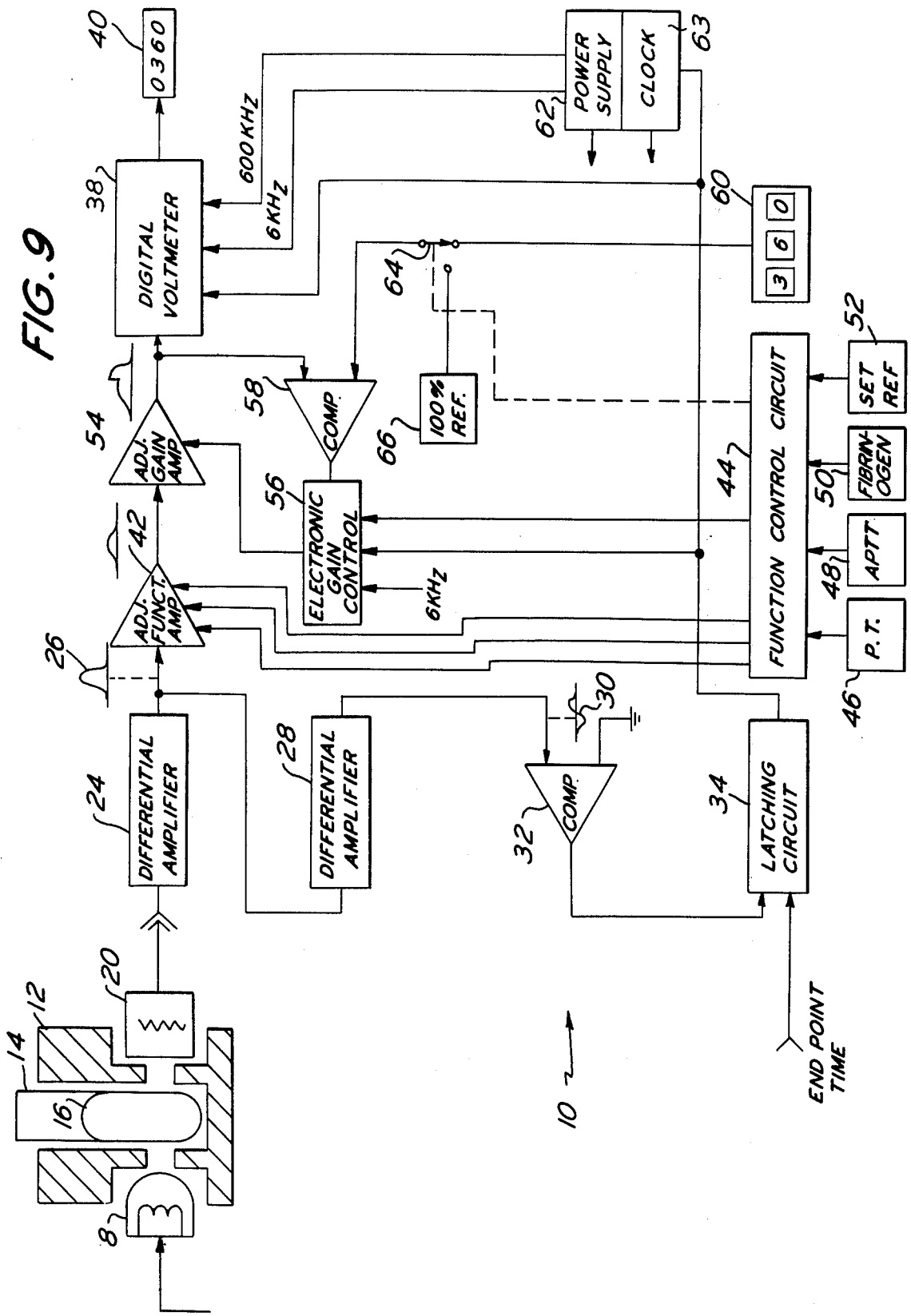
FIG. 9 is a schematic block diagram showing an apparatus for performing the present invention.

Referring now to FIG. 9, there is shown an apparatus 10 for determining clotting factor deficiencies in plasma. The circuit is designed to provide an output that can be read directly in two different units; milligrams per percent (mg/%) or milligrams per deciliter (mg/dl). Fibrinogen is the only factor which presently can be measured in units of weight rather than the relativistic percent activity for the remaining factors.

As shown, the apparatus 10 includes a support block 12 which may be provided with appropriate heating means to maintain the interior temperature thereof at 37° C. which is the temperature of human blood in the body and the proper temperature for evaluating blood plasma. As shown, a test tube 14 is mounted in the block 12 and contains therein a sample of plasma 16 which has been added to it by means of a pipette or other appropriate instrument for adding liquids in the proper quantity.

A light source 18 emits light having wave lengths which extend from the near infrared through the visible region of the electromagnetic spectrum. This light passes through the plasma 16 within the test tube 14 and is detected by the photodetector 20. The photodetector 20 may be of the photoresistive type, although other types of detectors can be used as appropriate to the electronic circuitry. The output of photodetector 20 may be conventionally processed by existing instruments such as the one described in U.S. Pat. No. 3,658,480. The signal appearing at the output of the photodetector 20 represents optical density (O.D.) as a function of time ($t$) as derived from a sample of blood plasma to which an appropriate reagent and/or calcium chloride have been added in correct quantities as described above.

The output of photodetector 20 is conducted to a differential amplifier 24 which differentiates the optical time-density signal to produce the electrical signal (dO.D./dt) at its output. This is the same signal that is shown in FIG. 1A, except its shape and amplitude may vary depending upon the plasma, the type of test (e.g., P.T. or A.P.T.T.) and the reagent used.

The output of differential amplifier 24 is conducted to differential amplifier 28 which again differentiates the signal using conventional circuitry to produce at its output the signal 30($d^2$O.D./$dt^2$) graphically illustrated adjacent to the output conductor. The reason for taking a second differential of the output of the photodetector 20 is to obtain the zero crossing point coincident with the peak value of the electrical signal 26. It will be recalled that this is the value which is being sought for performing the analysis herein described. It should be noted that the differential amplifier 28 is not being used in this case to determine the end point or clotting time. It merely determines the times of the peak value of a signal which, as those skilled in the art know, is when the slope changes sign.

The output of the differential amplifier 28 is applied to the comparator 32. The other input to the comparator 32 is a ground signal. Thus, for the circuit shown in FIG. 9, the zero point output of the differential amplifier 28 has been chosen as being ground.

When the signal output of differential amplifier 28 goes through the zero point, the output of comparator 32 changes. For example, it could be adjusted to change negatively from 5 volts to zero volts. This signal is applied to the latching circuit 34.

The latching circuit 34 is a flip-flop circuit. The other input to the latching circuit 34 is the end point time as derived from the circuit illustrated in U.S. Pat. No. 3,658,480. It will be recalled that the end point time is normally taken before the first differential signal reaches its peak value as indicated by the arrows in FIGS. 1A, 1B and 1C. This end point signal is used to reset the flip-flop of latching circuit 34 so that its output generates a signal that signals the rest of the circuit to commence looking for a peak value. The circuit knows that it has reached the peak amplitude when the latching circuit 34 receives a signal from the comparator 32. The purpose of this is so that the circuit does not look for the peak amplitude until high up on the ascending slope of the differential signal 26. This avoids any possibility of receiving a spurious peak signal.

The output of the latching circuit 34 is conducted to the electronic gain control circuit 56 and to the digital voltmeter 38 and both are turned on by the output. The electronic gain control circuit 56 is used to initially calibrate the instrument as hereinafter explained. Keeping in mind the explanation given above with respect to the determination of blood plasma factor deficiency, particularly in respect to FIGS. 7 and 8, it will be recalled that the unknown blood plasma sample is compared to a known standard to determine the blood plasma factor percent activity. In order to do this in the present instrument, it is necessary to first calibrate the instrument. The instrument must be calibrated each time the reagent or standard plasma is changed as well as when the instrument is first started up at the beginning of a testing period. This is because the reagents and the standard blood plasmas vary from lot to lot among manufacturers as well as from manufacturer to manufacturer. Indeed, a blood plasma or reagent derived from the same lot may vary from day to day due to changing environmental conditions.

In accordance with the present invention, the unknown is compared against a reference standard for determining fibrinogen in millgrams per percent or against a preset signal representative of 100% activity as explained hereinafter.

The electronic gain control 56 is a conventional "Tee" network used for feeding back a signal wth the vertical leg resistor being digitally selected for coarse and fine increments of gain. By way of example, the gain of the electronic gain control can be digitally selected from unity to five in 99 steps.

For purposes of determining fibrinogen in terms of milligrams per unit volume (e.g., mg/dl), the switch 50 marked fibrinogen is depressed thereby operating the function control circuit 44. This operates a relay which sets the switch 64 to the position shown in FIG. 9. In particular, it connects the comparator 58 to the digital dividers 60 which by means of a thumb wheel switch generates a signal proportional to the fibrinogen quantity in the control plasma. The fibrinogen content of plasma is stated on the label by the manufacturer. However, it could also be determined by chemical procedures. This value is set into the digital divider 60 through the thumb wheel switch. Moreover, this value therefore appears at one input of the comparator 58. This is done to regulate the circuit so that all subsequent tests of unknown plasmas can be measured against the standard quantity.

The set-reference switch is also depressed. It signals the circuit to calibrate on the first signal, but none thereafter as is explained more fully hereinafter.

The plasma 16 in the test tube 14 at this point in the circuit is the standard plasma. Thus, what in effect the circuit is doing is adjusting the incoming plasma signal to be equal to the reference set by the digital divider 60.

The operation of the fibrinogen switch 50 sets the adjustable function amplifier 42 at unity gain so that in effect it is not used for fibrinogen measurement. Thus, the signal 26 at its input is equal to the signal at its output. This makes the circuit measurement linear as required for fibrinogen measurement.

The gain of the adjustable gain amplifier 54 is set by the electronic gain control 56 and in particular by the value of its Tee network. It should be noted that the gain of the output of the differential amplifier 24 is relatively low and could never be equal to the output of the digital divider 60.

The signal from the latching circuit 34 starts the clock 63 to provide a clock signal for the electronic gain control 56. By way of example, the output of the clock 63 could be a 6 KHz signal although the frequency chosen for the clock is not particularly important. The clock 63 drives a pair of decade counters. This provides a BCD count of zero through nine for each of the counters. The effect is to provide 99 steps from the decoders. There are 19 resistance values in the Tee network (10 coarse and 9 fine value resistors). These 19 resistance values provide 99 discrete steps of gain for the adjustable gain amplifier 54.

From the foregoing, it should be apparent that what is happening is that the electronic gain control 56 is stepping up the gain of the adjustable gain amplifier 54 at a 6 KHz rate until its output is equal to the voltage set by the digital divider 60 as determined by the comparator 58. When the voltages at the input of the comparator 58 are equal, it generates a signal which removes the clock signal from the electronic gain control 56. At this point, the adjustable gain amplifier 54 has been set to deliver an output to the digital voltmeter 38 equal to the assay values set into the digital divider 60. This is confirmed by the display output 40 of the digital voltmeter 38 which should read the same as the values set into the digital divider 60.

Thereafter, the set reference switch 52 is depressed and the feedback network described above is no longer operative since the adjustable gain amplifier 54 has been set at the desired value.

The circuit is now read to test an unknown plasma sample for fibrinogen content. The procedure is the same as described above except the unknown plasma is now placed in a test tube 14 which in turn is inserted in a block 12. The circuit is operated as above and the peak point signal determined by use of the latching circuit 34. The output appearing on the display 40 of the digital voltmeter now reads fibrinogen content of the unknown directly in terms of milligrams per unit volume, e.g., milligrams per deciliter.

The foregoing describes the use of the circuit in FIG. 9 for determining fibrinogen. The circuit must be modified for doing factor assays with P.T. and A.P.T.T. end points as they are logarithmic rather than linear. In this instance, either the P.T. switch 46 or the A.P.T.T. switch 48 is depressed. This causes function control circuit 44 to move the switch 64 by means of a relay over to connect it to the 100% reference source 66. This is an adjustable voltage value set into the comparator 58. The 100% reference 66 is a voltage source which is determined to be a 100% value, keeping in mind that P.T. and A.P.T.T. tests, assay blood plasma for factor deficiencies according to the relativistic percent activity values. This is based upon a normal control plasma deemed to have 100% activity of all factors. To calibrate the circuit, a standard plasma having a known normal factor level is placed in the test tube 14 and allowed to clot in accordance with either a P.T. test system or an A.P.T.T. test system as desired. The set reference switch 52 is depressed. This sets the value of the adustable gain amplifier at the 100% level as determined by the 100% reference voltage source 66. Thus, the digital voltmeter 38 reads out the 100% reference voltage. The adjustable funtion amplifier 42 is now brought into operation. It will be recalled that the apparently linear relation shown in FIGS. 6 and 8 and described by formula (1) is really a logarithmic function. Stated otherwise, the peak heights of the first differential of the optical density-time curve is a logarithmic function not a linear function. If the peak heights shown in FIGS. 6 and 8 were plotted on linear graph paper rather than log log paper, they would be exponential.

The purpose of the adjustable function amplifier 42 therefore is to convert the differential input signal 26 to a logarithmic function, which it does. The form of the logarithmic function depends upon the values of N, Y and C which in turn depend upon whether a P.T. or A.P.T.T. test is being made. Since logarithmic converting circuits are well known, the adjustable function amplifier 42 need not be described in detail.

Once the circuit has been calibrated using a standard plasma, the percent of activity level is thereafter determined by placing diluted plasma in the ratios described above in the block 12 and recording their outputs in the display 40. Once the circuit has been standardized, all unknown blood plasmas can be tested and read directly in percent activity. Thus, there is no need to make graphical plots.

Figure 10:
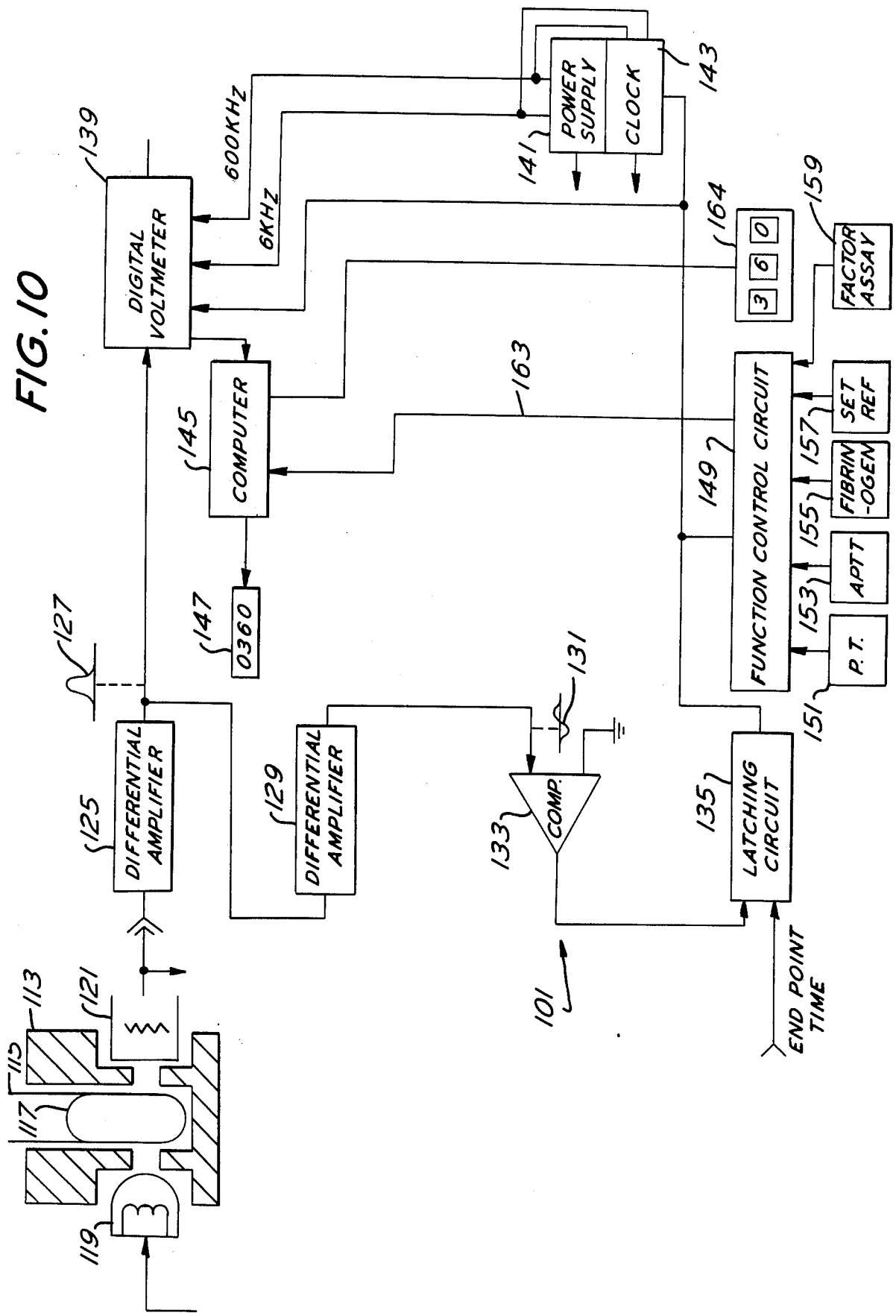
FIG. 10 is a schematic block diagram showing another apparatus for performing the present invention.

Referring now to FIG. 10, there is shown another form of the invention in which factor assays and fibrinogen content measurements can be made using a computer. In addition, the apparatus embodied in FIG. 10 can be used to effect differential detection of factor deficiencies by comparison of peak amplitudes of the P.T., the A.P.T.T. and the T.T. tests as explained in more detail hereinafter.

The apparatus shown in FIG. 10 is designated generally as 101 and includes a support block 113 which may be provided with appropriate heating means to maintain the interior temperature thereof at 37° C. which is the temperature of human blood in the body and the proper temperature for evaluating blood plasma. A test tube 115 is mounted in the block 113 and contains therein a sample of plasma 117 which has been added to it by means of a pipette or other appropriate instrument for introducing liquids in the proper quantity.

A light source 119 emits light having wave lengths which extend from the near infrared through the visible region of the electromagnetic spectrum. This light passes through the plasma 117 within the test tube 115 and is detected by the photodetector 121. The photodetector 121 may be of the photoresistive type, although other types of detectors can be used as appropriate to the electronic circuitry and the wave lengths of the radiation incident upon it. The output of the photodetector 121 may be processed by existing instruments such as the one described in U.S. Pat. No. 3,658,480 for determining the clotting (end point) time of the plasma. The signal appearing at the output of the photodetector 121 represents the optical density as the function of time as derived from a sample of blood plasma to which an appropriate reagent and/or calcium chloride have been added in correct quantities as described heretofore.

The output of photodetector 121 is conducted to a differential amplifier 125 which differentiates the optical density-time signal to produce the electrical signal 127 at its output. This is the same signal that is shown in FIG. 1A, except its shape and amplitude may vary depending upon the plasma, the type of test (e.g., P.T., T.T. or A.P.T.T.) and the reagent used.

The output of differential amplifier 125 is conducted to differential amplifier 129 which again differentiates the signal using conventional circuitry to produce at its output the signal 131 graphically illustrated adjacent the output conductor. The reason for taking a second differential output of the photodetector 121 is to obtain the zero crossing point coincident with the peak value of the electric signal 127. It will be recalled that this is the value which is being sought for performing the analysis herein described. It should be noted that the differential amplifier 129 is not being used to determine the end point of clotting time. It merely determines the peak value of a signal which, as those skilled in the art know, is when the slope changes sign.

The output of the differential amplifier 129 is applied to the comparator 133. The other input to commparator 133 is a ground signal. Thus, for the circuit shown in FIG. 10, the zero point output of the differential amplifier 129 has been chosen as being ground.

When the signal ouput of differential amplifier 129 goes through the zero point, the output of comparator 133 changes. For example, it could be adjusted to change negatively from 5 volts to zero volts. This signal is applied to the latching circuit 135. Latching circuit 135 is a flip-flop circuit. The other input to the latching circuit 135 is the end point time as derived from the circuit illustrated in U.S. Pat. No. 3,658,480 or other circuitry for measuring that value. It will be recalled that the end point time is normally taken before the first differential signal reaches its peak value as indicated by the arrows in FIGS. 1A, 1B and 1C. This end point signal is used to reset the flip-flop of latching circuit 135 so that its output generates a signal that signals the rest of the circuit to commence looking for a peak value. The circuit knows that it has reached the peak amplitude when the latching circuit 135 receives a signal from the comparator 133. The purpose of this is to prevent the circuit from detecting spurious peak signals. This is accomplished by inhibiting the circuit so that it does not seek to detect the peak amplitude until high up on the ascending slope of the differential signal 127.

The output of the latching circuit 135 is conducted to the digital voltmeter 139 to turn it on.

The apparatus illustrated in FIG. 10 is also provided with a power supply 141 and clock 143 for providing clock signals and appropriate voltages to the various circuit elements. If desired, the clock 143 or one or more of the clocking signals generated by it may be controlled by the output of latching circuit 135.

From the foregoing, it can be observed that the digital voltmeter 139 is controlled so that it generates a digital output equal to the peak vaue of the differential signal 127 which electronically is a voltage. This output is transferred into memory in the computer 145. If desired, the computer 145 can also display the peak value on display means 147. If desired, alternate or duplicate display means connected directly to the digital voltmeter 139 can also be provided as well as to the computer 145.

Computer 145 is programmed to perform factor assays, fibrinogen quantitations and differential detection of factor deficiencies described hereinafter. By way of example, but not limitation, the computer 145 could be a Fairchild PPS 25 which is a mask programmable mini-computer. While this computer is capable of performing all of the functions described hereinafter, it should be understood that other presently available mini-computers can also be used and it is anticipated that certain types of micro-computers presently being developed will also be capable of performing the functions hereinafter described.

The apparatus 101 also includes a function control circuit 149 which provides appropriate switching circuitry for selecting the mode or function of the computer 145 and interfacing the mode select switches 151, 153, 155, 157, and 159 to the computer 145 through the cable 163. Although illustrated as a single line, it should be recognized that each of the conductors such as 163 may in fact be a plurality of conductors for transferring electronic signals from one circuit function device to another.

Also connected to the computer 145 is the digital encoder 164 which by means of thumb wheel switches can be set to generate a BCD signal equal to the fibrinogen assay value as more particularly explained hereinafter.

The manner in which the apparatus 101 can be used for performing factor assays is as follows. The exponential relationship between percent activity of a given factor in a plasma and the clotting time of that plasma has been documented previously in this application. This relationship holds true for factor assays of the intrinsic factors VIII, IX, XI and XII using the activated partial thromboplastin test (A.P.T.T.) as well as the extrinsic factors II, V, VII and X by the prothrombin time test (P.T.). As shown in FIG. 8, a plot of the assay value on log log paper with time being the "Y" or vertical axis and percent activity being the "X" or horizontal axis provides a straight line. The unknown or patient plasma can be assayed by determining where it fits on this line. The problem with a clotting time assay is that it loses sensitivity somewhere between approximately 1 and 6% activity. As a result, several dilutions must be run so that data points of higher factor levels may be used to find the slope of the line.

In accordance with the present invention, the log of the peak value of the first derivative of the change in optical density has been found to be proportional to the log of the level of various clotting factors in the plasma. As a result, it has been found that by using the assay procedures described previously, the amplitude of the first derivative varies as a function of the percent activity of the assayed factor present in the plasma, since the level of all other factors is normal in the deficient substrate plasma. In particular, the peak amplitude of the first derivative varies exponentially and in the same sense as the level of the factor of interest; e.g., (high amplitude = high level, low amplitude = low level without direct relationship to the clotting time).

As previously stated, one of the major advantages resulting from this is that the relationship holds to approximately 1.5% activity whereas the same test using time loses sensitivity at approximately 6% activity. Indeed, for some factors, the peak value versus percent activity relationship can be verified down to factor levels of less than 0.1%. Since the amplitude of the first derivative of optical density on a log scale holds its proportional relationship over this wide range of factor activity levels on a log scale, it is no longer necessary to run intermediate dilutions of plasma to accurately establish the slope of the straight line curve. Therefore, two widely separated peak values ($A_1$ and $A_2$, below) can be validity selected.

It has already been explained how the apparatus 101 shown in FIG. 10 measures the peak amplitude of the first differential optical density in the digital voltmeter 139 and also that this peak value is gated into the computer 145. This peak value and others as explained below is stored in the computer memory which then processes the information and ultimately displays the percent factor activity of the plasma being tested without plotting any information on log log graph paper.

To find the percent factor activity level of an unknown plasma, the apparatus 101 must fist establish the slope of the logarithmic relationship:

$$\text{Log } A = \text{Log } A_1 + \left\{ \text{Log}\left(\frac{V}{V_1}\right) \left[ \frac{\text{Log}\left(\frac{A_2}{A_1}\right)}{\text{Log}\left(\frac{V_2}{V_1}\right)} \right] \right\} \quad (2)$$

where:
A = percent factor activity level of the unknown (which is equal to the Antilog of log A)
V = peak amplitude of dO.D./dt of the unknown plasma (voltage)
$A_1$ = known factor activity level of a first standard blood plasma (e.g., 0.1%; log 0.1 = −1)
$V_1$ = peak amplitude of dO.D./dt of $A_1$ (voltage)

$A_2$ = factor activity level of a second standard blood plasma (e.g., 100%; log 100 = 2)
$V_2$ = peak amplitude of dO.D./dt of $A_2$ (voltage)

Formula (2) is derived from formula (1).

Given the foregoing assigned values for $A_1$ and $A_2$, the formula for A (percent factor activity of the unknown plasma sample) can be simplified as follows:

$$A = \text{Antilog}\left\{ \text{Log}\left(\frac{V}{V_1}\right) \left[ \frac{3}{\log\left(\frac{V_2}{V_1}\right)} \right] \right\} - 1 \quad (3)$$

$$A = \text{Antilog } (\text{Log } V - \text{Log } V_1)\left( \frac{3}{\log V_2 - \log V_1} \right) - 1 \quad (4)$$

As explained above, the wide range over which the relationship of the formula (2) holds permits the selection of 100% factor activity and 0.1% factor activity for the purpose of establishing the slope of the curve. Moreover, it permits the slope of the curve to be established using only two such points. This is done in the apparatus 101 by running two control plasmas with known factor activity levels, one being the 100% normal plasma and the other being the deficient substrate plasma which has a value of 0.1% factor activity. The peak amplitude of the first derivative of these two control plasmas is unknown because it is affected by the type of reagents used and will vary with different factor assays. However, the reagents only cause a difference in the offset value which may be described from a graphical point of view as the "Y" or vertical axis offset. The same plasmas run with different reagents will generate parallel straight lines on a log log graph. Therefore, once the peak amplitude value for 100% factor activity and 0.1% factor activity have been stored in the computer memory, it becomes a straightforward matter of solving formula (4) to determine percent activity of the unknown plasma by detecting the peak amplitude of the first differential of its optical density as a voltage and entering it into the computer via the output of the digital voltmeter 139.

The process for using the apparatus 101 includes depressing the factor assay button 159 therefore setting the computer through the function control circuit into a factor assay mode. Thereafter, the 10% factor activity control plasma is run through the instrument, preferably in duplicate as explained below. This is accomplished by inserting the test tube 115 containing the plasma 117 in the block 113. Thereafter the reagent is added and the pipette removed. The test proceeds until the peak value of the first differential ($V_2$) is determined by the digital voltmeter 139 and stored in the memory in computer 145.

The second step is to run the 0.1% factor activity substrate control plasma, again in duplicate and in the manner explained above. This value ($V_1$) is entered into the computer. Thereafter, the unknown sample(s) plasma can be tested.

The program for solving formula (4) for (A) is straightforward and need not be described in detail herein. Programs already exist for solving logarithmic functions and therefore any program which is suitable can be used.

As indicated above, good clinical procedure dictates that all samples and the unknown should be run in duplicate, and the average taken. Therefore, formula (4) and the computer program should be modified as follows:

$$V = \left(\frac{V' + V''}{2}\right) \quad (5)$$

$$V_1 = \left(\frac{V_1' + V_1''}{2}\right) \quad (6)$$

$$V_2 = \left(\frac{V_2' + V_2''}{2}\right) \quad (7)$$

where a prime (') indicates the first sample and a double prime (") indicates the second sample.

A fibrinogen assay can be performed using the apparatus 101 as follows. As previously stated, the relationship between the peak amplitude of the first derivative of the optical density and the quantity of fibrinogen in the plasma using thrombin reagent, is linear. By way of example, if a peak amplitude of 3 volts (V) = 300 mg/dl fibrinogen then a peak amplitude of 4 volts (V) will equal 400 mg/dl fibrinogen.

To perform the fibrinogen determination with the apparatus 101, the buttom 155 is depressed thereby setting the computer in a fibrinogen assay mode. Thereafter, a control plasma which has been assayed for fibrinogen is run through the apparatus 101 as follows:

The assayed value of the fibrinogen is set by thumb wheel switch into the divider 164. This value is transferred into the memory of computer 145 memory by means of the set reference button 157. Then a control plasma is run through the apparatus 101 to determine its peak value. The control plasma is run in duplicate. This procedure establishes the multiplier to be applied to all subsequent plasmas run against the control plasma. Thus, the basic formula for fibrinogen is:

$$CV = F \quad (8)$$

where:
C = constant
V = peak amplitude of the first derivative in volts
F = mg/dl fibrinogen.
For duplicate samples:

$$V = \left(\frac{V' + V''}{2}\right) \quad (9)$$

where:
V' = first sample
V'' = second sample.

To set the computer, "C" must be determined as a function of $F_1$ which is the reference fibrinogen value in mg/dl set in through divider 164.
Accordingly, $$\text{Accordingly, } C = F_1 \left(\frac{1}{\frac{V' + V''}{2}}\right) \quad (10)$$

Once C has been determined and set into the computer, F (fibrinogen) for the unknown plasma can be determined according to the formula:

$$F = C\left(\frac{V' + V''}{2}\right) \quad (11)$$

As each of the foregoing formulas is linear, the preparation of an appropriate program for the computer 145 is straight-forward and therefore need not be described in detail.

The apparatus 101 can also be used to perform differential detection of factor deficiencies. As indicated above, differential comparison between various tests permits the clinician to establish which particular factor or group of factors is deficient. It will be recalled that most of the tests (e.g., P.T. and A.P.T.T.) are specific to more than one clotting factor, except for the thrombin test which is specific for fibrinogen only (factor I). Therefore, differential comparisons between the tests are undertaken to determine which individual factor or group of factors is deficient. This is best illustrated by reference to the three most commonly used hospital admission or presurgical screening situations. The prothrombin time test (P.T.) is specific for factors II, V, VII and X. The activated partial thromboplastin time test (A.P.T.T.) is specific for factors II, V, VIII, IX, X, XI and XII. both of the foregoing tests are affected by the amount of factor I (fibrinogen) present. The thrombin time test (T.T.) is specific to factor I only.

As has previously been noted, these are time tests. However, the peak amplitude of the first differential of these tests provide additional information about the plasma than cannot be obtained from clotting time alone. The comparison of the peak amplitudes of the P.T. and the A.P.T.T. tests provides an additional screening parameter than is more sensitive to mild deficiencies in the intrinsic clotting system than the clotting time. This comparison is also sensitive to deficiencies in the extrinsic clotting system.

Both the P.T. and the A.P.T.T. test amplitudes are sensitive to fibrinogen (factor I). The amount of fibrinogen in the plasma will affect the amplitude of the first differential curve; e.g., (high fibrinogen = high amplitude, low fibrinogen = low amplitude), and in most instances the amplitude variation as a function of fibrinogen, particularly at high levels, is not detectable by measuring clotting time. The clotting times for most mild factor deficiencies are in the "normal" to "boarderline" range and are of little or no help in diagnosis. However, differential comparison of the peak amplitudes of the P.T. and the A.P.T.T. tests of a plasma will easily detect mild factor deficiency and indicate whether it is in the intrinsic or extrinsic clotting system.

Figure 11:
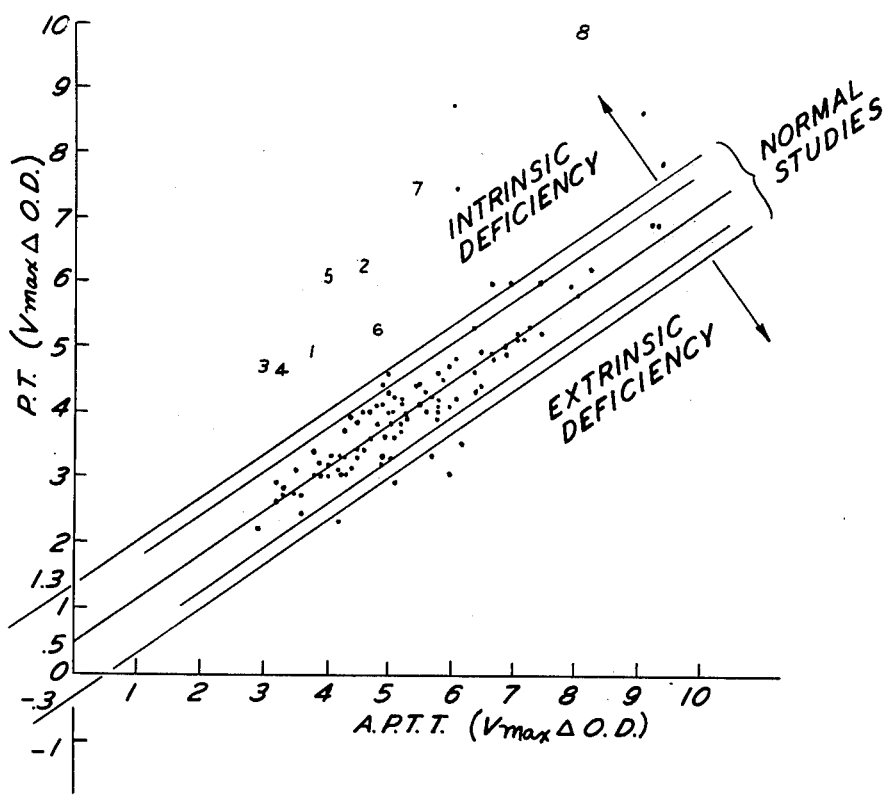
FIG. 11 is a scattergram relating to peak value of first differential of optical density of the A.P.T.T. and P.T. tests.

This is accomplished by first establishing the ratio of P.T. amplitude to A.P.T.T. amplitude for a large number of normal plasmas. Graphically, the P.T. amplitude can be plotted on the "Y" (vertical) axis of a linear graph and the A.P.T.T. amplitude of the same plasma on the "X" (horizontal) axis. Due to the variation in fibrinogen level, these data points will fall about a regression line on the scattergram thus produced. FIG. 11 shows an example of such a scattergram based on 100 normal plasmas. FIG. 11 is a scattergram which relates to peak value of the first differential of optical density (V max Δ O.D.) of the A.P.T.T. and the P.T. in normal subjects (dots) and eight patients with isolated, mild factor VIII deficiency (case numbers). The central regression line is bracketed by 95 and 97%. confidence belt. Standard deviation for a regression is 0.23. The slope of the regression line in FIG. 11 is 0.65.

From a scattergram such as is shown in FIG. 11, it is possible to derive the formulas for comparison of the P.T. and A.P.T.T. tests and arrive at one of three conclusions:
1. Normal
2. Intrinsic deficiency
3. Extrinsic deficiency.

The presence of either 2 or 3 would suggest that further studies be done to isolate the particular factor deficiency.

The basic formula for the regression line is:

$$Y = MX + B = Y - B/M \qquad (12)$$

where
Y = P.T. peak amplitude (Voltage)
M = slope of regression
X = A.P.T.T. peak amplitude (Voltage)
B = Offset.

The foregoing formula (12) is used to define the bounds for 1 — "Normal", 2 — "Intrinsic deficiency" and 3 — "Extrinsic deficiency". All amplitudes referred to are peak amplitudes of the first differential of the optical density.

Using the scattergram of FIG. 11, we obtain the following:
1. If $Y \leq 0.65 X + 1.3$ and $\geq 0.65 X - 0.3$ = normal studies
2. If $Y > 0.65 X + 1.3$ = intrinsic deficiency
3. If $Y < 0.65 X - 0.5$ = extrinsic deficiency The slope (M) and the offset (B are a function of the A.P.T.T. reagent used and to some extent the thromboplastin in the P.T. test. Therefore, these two parameters (M and B) must be defined by running many normal plasmas with the various reagents commonly used. Once defined these constants can be switch selectable in the computer 145 of the apparatus 101. This is provided by the switches 151 and 153 as indicated. Summarizing then, parameters M and B are established by prior testing and the values are set into the instrument 101 as preset references.

As previously indicated, clotting factors I, II, V and X have an effect on both the P.T. and the A.P.T.T. tests. Factor I, fibrinogen, concentration cannot generally be detected by differential comparison of the P.T. and the A.P.T.T. tests. Factors II, V and X, however, definitely affect the amplitude of the P.T. and A.P.T.T. tests, and with similar reduction in their peak amplitudes, may show up as "normal studies". For the foregoing reasons, a differential comparison between the P.T. and the thrombin time test (T.T.) and a differential comparison betwen the A.P.T.T. and the T.T. test is performed. The same formula as above (12) is used for these comparisons. However, the results are derived as follows:

P.T. vs. T.T. = Normal or Extrinsic Deficiency
A.P.T.T. vs. T.T. = Normal or Intrinsic Deficiency.

Since factors V and X affect both P.T. and the A.P.T.T., a deficiency in these factors can be detected since they will show as both intrinsic and extrinsic deficiencies. Thereafter, normal correction studies can be used to differentiate factors V and X as well as define any other factor deficiency.

The use of the apparatus 101 for the differential comparison of the peak amplitudes of the first differential of the optical density of the above differential screening tests is described below. This provides a test system which is much more sensitive to mild factor deficiencies than clotting time alone.

The procedure for using the instruments is to determine the slope M and the offset B according to the reagent selected. Thereafter, all of the plasmas to be tested are assigned a sequence number. Then the P.T. mode function 151 is depressed and the peak amplitude of each of the several plasmas is sequentially run in duplicate and the average peak value stored in the memory of the computer 145. Thereafter, the A.P.T.T. mode functions 153 is depressed and the same plasms are run through the instrument in the same sequence and in duplicate. As the data from the A.P.T.T. test becomes available, it is compared by the computer with the stored data from the P.T. tests. This result is made in accordance with the formula (12). If there be an extrinsic or an intrinsic deficiency. it is displayed or printed out if desired.

Figure 12:
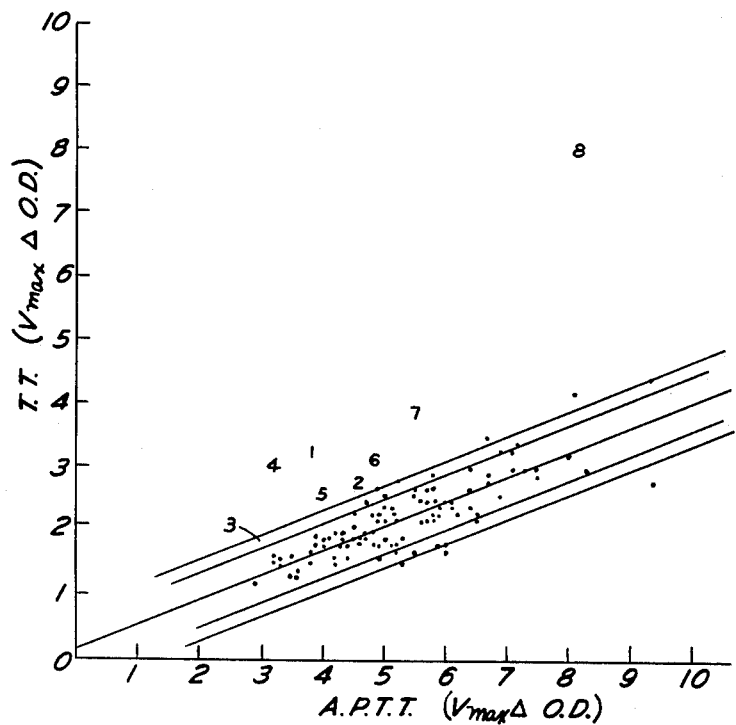
FIG. 12 is a scattergram relating the peak value of the first differential of optical density of the A.P.T.T. and T.T. tests.

The same procedure could be used to compare T.T. vs. P.T. and T.T. vs. A.P.T.T. tests. By way of example, FIG. 12 is a scattergram relating the peak value of the first differential of optical density of the A.P.T.T. and T.T. in normal subjects (dots) and eight patients with isolated, mild factor VIII deficiency (case numbers). The central regression line is bracketed by 95 and 97% confidence belts. Standard deviation from regression is 0.20. Again, the programming of the computer according to the foregoing formulas is straightforward, particularly since they are linear formulas, and need not be described in detail.

The present invention may be embodied in other specific forms without departing from the spirit or essential attributes thereof and, accordingly, reference should be made to the appended claims, rather than to the foregoing specification as indicating the scope of the invention.

We claim:
1. A method of determining clotting factor levels (other than fibrinogen) in blood plasma, comprising the steps of:
generating an electric signal proportional to the optical density of an unknown blood plasma undergoing clotting over a period of time;
electronically differentiating said optical density-time signal to generate a first differential signal;
electronically determining the peak value of said first differential signal; and, to determine clotting factor level activity of the unknown plasma;
electronically comparing said peak value to a predetermined standard logarithmic function based on standard plasmas having known factor activity levels, said standard logarithmic function relating the peak values of the first differential of the optical density-time signal of said standard plasmas to corresponding known factor activity levels.
2. A method of determining clotting factor levels (other than fibrinogen) in blood plasma, comprising the steps of:
generating an electrical signal proportional to the optical density of a first standard blood plasma undergoing clotting over a period of time, said first standard bloos plasma having a known factor activity level ($A_1$);

electronically differentiating said first standard optical density-time electric signal to generate a first standard differential signal;

electronically determining the peak value ($V_1$) of said first standard first differential signal;

generating an electric signal proportional to the optical density of a second standard blood plasma undergoing clotting over a period of time, said second standard blood plasma having a known factor activity level ($A_2$) different from the factor activity level of said first standard blood plasma;

electronically differentiating said second standard optical density-time electrical signal to generate a second standard first differential signal;

electronically determining the peak value ($V_2$) of said second standard first differential signal;

electronically determining the slope of the logarithmic relationship:

$$\text{Log } A = \text{Log } A_1 + \left\{ \text{Log}\left(\frac{V}{V_1}\right)\left[\frac{\text{Log}\left(\frac{A_2}{A_1}\right)}{\text{Log}\left(\frac{V_2}{V_1}\right)}\right]\right\}$$

where:
A = percent factor activity of the unknown blood plasma (which is equal to the Antilog of log A)
V = peak amplitude of dO.D/dt of the unknown plasma (voltage)
$A_1$ = factor activity level of first standard plasma
$V_1$ = amplitude of dO.D./dt of $A_1$ (voltage)
$A_2$ = factor activity level of second standard plasma
$V_2$ = peak amplitude of dO.D./dt of $A_2$ (voltage).

generating an electric signal proportional to the optical density of an unknown blood plasma undergoing clotting over a period of time;

electronically differentiating said optical density-time electric signal to generate a first differential signal for said unknown blood plasma;

determining the peak value (V) of said first differential signal for said unknown blood plasma; and electronically comparing the peak value (V) of the unknown blood plasma with the slope of said logarithmic relationship to determine the factor activity level (A) in the unknown plasma.

3. A method of determining clotting factor levels (other than fibrinogen) in blood plasma in accordance with claim 2 wherein the value of $A_1$ is selected as 0.1% factor activity level and the value of $A_2$ is selected as 100% factor activity level.

4. A method of making differential detection of factor activity level to detect mild factor activity level deficiencies in the intrinsic or extrinsic clotting system, comprising the steps of:

electronically sequentially determining the peak values of the first differential of the optical density of a series of known activity level blood plasmas undergoing clotting over a period of time pursuant to a first clotting test procedure;

electronically sequentially determining the peak value of the first differential of the optical density of said known activity level blood plasmas undergoing clotting over a period of time pursuant to a second clotting test procedure;

electronically comparing the peak values of the first test procedure to the peak values of the second test procedure to determine the slope of a statistical regression line;

electronically determining the peak value of the first differential of the optical density of an unknown blood plasma and comparing it with the slope of the regression line to determine whether said unknown plasma falls within the statistical normal range, the statistical intrinsic deficiency range, or the statistical extrinsic deficiency range.

5. A method for making differential detection of factor activity level in accordance with claim 4 wherein the first clotting test is the activated partial thromboplastin time test and the second clotting test procedure is the prothrombin time test.

6. A process in accordance with claim 4 wherein the first clotting test procedure is the activated partial thromboplastin test and the second clotting test procedure is the thrombin time test.

7. A method for making differential detection of factor activity levels in accordance with claim 4 wherein the first clotting test procedure is the partial thromboplastin test and the second clotting test procedure is the thrombin test.

8. A method of determining clotting factor levels (other than fibrinogen) in blood plasma, comprising the steps of:

generating an electrical signal proportional to the optical density of a first standard blood plasma undergoing clotting over a period of time, said first standard blood plasma having a known factor activity level;

electronically differentiating said first standard optical density-time electrical signal to generate a first standard differential signal;

electronically determining the peak value of said first standard first differential signal;

generating an electric signal proportional to the optical density of a second standard blood plasma undergoing clotting over a period of time, said second standard blood plasma having a known factor activity level different from the factor activity level of said first standard blood plasma;

electronically differentiating said second standard optical density-time electrical signal to generate a second standard first differential signal;

electronically determining the peak value of said second standard first differential signal;

electronically determining the slope of the logarithmic function relating said standard peak values to the first and second known standard activity levels;

generating an electrical signal proportional to the optical density of an unknown blood plasma undergoing clotting over a period of time, said unknown blood plasma having an unknown factor activity level which is to be determined;

electronically differentiating said unknown optical density-time electrical signal to generate a first differential signal for said unknown blood plasma;

electronically determining the peak value of said first differential signal for said unknown blood plasma; and electronically comparing this peak value of the first differential for said unknown blood plasma with the slope of said logarithmic relation to determine the factor activity level of the unknown plasma.

9. Apparatus for determining fibrinogen levels in blood plasma in weight per unit volume, comprising:

electronic means for generating an electrical signal proportion to the optical density of a blood plasma undergoing clotting over a period of time, said blood plasma having an unknown fibrinogen level as measured in weight per unit volume;

electronic means for differentiating said optical density-time electrical signal to generate a first differential signal;

electronic means for determining the peak value of said first differential signal, said peak value being directly proportional to the fibrinogen level in said unknown blood plasma as measured in weight per unit volume;

and electronic means for calibrating said peak value determining means, said calibrating means including amplifier means for amplifying said first differential signal, and means for electronically adjusting the gain of said amplifier means to a value determined by a standard plasma with a known fibrinogen level.

10. Apparatus for determining clotting factor levels (other than fibrinogen) in blood plasma, comprising:

electronic means for generating an electric signal proportional to the optical density of an unknown blood plasma undergoing clotting over a period of time;

electronic means for differentiating said optical density-time electric signal to generate a first differential signal;

electronic means for determining the peak value of said first differential signal; and, as a means for determining the clotting factor activity level in the unknown plasma:

electronic means for electronically comparing said peak value to a standard logarithmic function relating the predetermined peak values of the first differential of the optical density-time signal of standard plasmas undergoing clotting over a period of time to the known activity levels of said standard plasmas; and means for determining and reading our from such comparison the clotting factor activity level of the unknown plasma.

11. Apparatus for determining clotting factor levels (other than fibrinogen) in blood plasma, comprising:

means for generating an electric signal proportional to the optical density of the unknown blood plasma undergoing clotting over a period of time;

means for electronically differentiating said optical density-time signal to generate a first differential signal;

means for determining the peak value of the first differential signal; and, as means for determining the factor activity level of the unknown plasma;

means for electronically determining the peak value of a differential electrical signal representative of the first differential of the optical density of a first standard blood plasma undergoing clotting over a period of time, said first standard blood plasma having a known factor activity level;

said last above means being usable for electronically determining the peak value of a differential electrical signal representative of the first differential of the optical density of a second standard blood plasma undergoing clotting over a period of time, said second standard blood plasma having a known factor activity level different from the factor activity level of the first standard blood plasma;

means for determining the slope of a logarithmic function relating said first and second standard peak values to the known factor activity levels of said first and second standard blood plasmas;

means for comparing the peak value of the unknown blood plasma with the slope of said logarithmic function; and means for determining and reading from said comparison the factor activity level in the unknown plasma.

12. Apparatus for making differential detection of factor activity levels to detect mild factor activity level deficiencies in the intrinsic or extrinisic clotting system, comprising the steps of:

electro-optical means for sequentially determining the peak values of the first differential of the optical density of a series of known activity level blood plasmas undergoing clotting over a period of time pursuant to a first clotting test procedure;

the last said electro-optical means also being used for sequentially determining the peak values of the first differential of the optical density of said known activity level blood plasmas undergoing clotting over a period of time pursuant to a second clotting test procedures;

electrical means for comparing the peak values determined by the first test procedure to the peak values determined by the second test procedure to determine the slope of a statistical regression line;

electrical means for determining the peak value of the first differential of the optical density of an unknown blood plasma and electrical means for comparing it with the slope of the regression line to determine whether said unknown plasma falls within the statistical normal range, statistical intrinsic deficiency range, or the statistical extrinsic deficiency range.

* * * * *